United States Patent
Murugesan et al.

(10) Patent No.: US 6,673,824 B1
(45) Date of Patent: Jan. 6, 2004

(54) PHENYL SULFONAMIDE ENDOTHELIN ANTAGONISTS

(75) Inventors: Natesan Murugesan, Lawrenceville, NJ (US); John T. Hunt, Princeton, NJ (US); Philip D. Stein, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/552,543

(22) Filed: Apr. 19, 2000

Related U.S. Application Data

(63) Continuation of application No. 08/584,767, filed on Jan. 11, 1996, now Pat. No. 6,107,320, which is a continuation of application No. 08/146,262, filed on Oct. 29, 1993, now Pat. No. 5,514,696, which is a continuation-in-part of application No. 08/041,583, filed on Apr. 13, 1993, now abandoned, which is a continuation-in-part of application No. 08/021,410, filed on Feb. 23, 1993, now abandoned, which is a continuation-in-part of application No. 07/879,000, filed on May 6, 1992, now abandoned.

(51) Int. Cl.[7] ............................................. A61K 31/42
(52) U.S. Cl. ....................................... 514/379; 514/380
(58) Field of Search .................................. 514/379, 380

(56) References Cited

U.S. PATENT DOCUMENTS

| | | | | |
|---|---|---|---|---|
| 5,846,985 A | * | 12/1998 | Murugesan | 514/364 |
| 5,939,446 A | * | 8/1999 | Murugesan et al. | 514/380 |
| 6,080,774 A | * | 6/2000 | Murugesan et al. | 514/380 |

* cited by examiner

Primary Examiner—Fiona T. Powers
(74) Attorney, Agent, or Firm—Stephen B. Davis

(57) ABSTRACT

Compounds of the formula

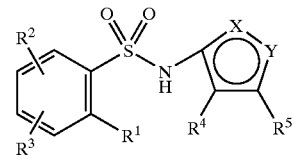

inhibit the activity of endothelin. The symbols are defined as follows:

$R^1$, $R^2$ and $R^3$ are each independently
  (a) hydrogen, except that $R^1$ is other than hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2$$R^6$;
  (i) —SH, —S(O)$_n$$R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7$$R^8$; or
  (k) —$Z^4$—N($R^{11}$)—$Z^5$—N$R^9$$R^{10}$;

and the remaining symbols are as defined in the specification.

4 Claims, No Drawings

PHENYL SULFONAMIDE ENDOTHELIN ANTAGONISTS

This application is a continuation of U.S. application Ser. No. 08/584,767 filed Jan. 11, 1996, now U.S. Pat. No. 6,107,320, which is a continuation of U.S. application Ser. No. 08/146,262, filed Oct. 29, 1993, now U.S. Pat. No. 5,514,696 which a continuation-in-part of U.S. application Ser. No. 08/041,583 filed Apr. 13, 1993, now abandoned, which is a continuation-in-part of U.S. application Ser. No. 08/021,410 filed Feb. 23, 1993, now abandoned, which is a continuation-in-part of U.S. application Ser. No. 07/879,000 filed May 6, 1992 now abandoned.

FIELD OF THE INVENTION

This invention relates to endothelin antagonists useful, inter alia, for treatment of hypertension.

BRIEF DESCRIPTION OF THE INVENTION

Compounds of the formula

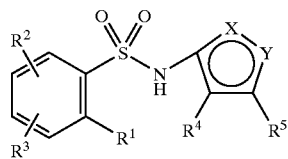

and pharmaceutically acceptable salts thereof are endothelin receptor antagonists useful, inter alia, as antihypertensive agents. Throughout this specification, the above symbols are defined as follows:

one of X and Y is N and the other is O;

$R^1$, $R^2$ and $R^3$ are each independently
  (a) hydrogen, except that $R^1$ is other than hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7 R^8$; or
  (k) —$Z^4$—N($R^{11}$)—$Z^5$—N$R^9 R^{10}$;

$R^4$ and $R^5$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7 R^8$;
  (k) —$Z^4$—N($R^{11}$)—$Z^5$—N$R^9 R^{10}$; or
  (l) $R^4$ and $R^5$ together are alkylene or alkenylene (either of which may be substituted with $Z^1$, $Z^2$ and $Z^3$), completing a 4- to 8-membered saturated, unsaturated or aromatic ring together with the carbon atoms to which they are attached;

$R^6$ is alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^7$ is
  (a) hydrogen;
  (b) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
  (c) cyano;
  (d) hydroxyl;
  (e) —C(O)H or —C(O)$R^6$;
  (f) —CO$_2R^6$;
  (g) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$, except when $Z^4$ is —S(O)$_n$—;

$R^8$ is
  (a) hydrogen;
  (b) —C(O)H or —C(O)$R^6$, except when $Z^4$ is —C(O)— and $R^7$ is —C(O)H, —C(O)$R^6$ or —CO$_2R^6$;
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$; or $R^7$ and $R^8$ together are alkylene or alkenylene (either of which may be substituted with $Z^1$, $Z^2$ and $Z^3$), completing a 3- to 8-membered saturated, unsaturated or aromatic ring together with the nitrogen atom to which they are attached;

$R^9$ is
  (a) hydrogen;
  (b) hydroxyl;
  (c) —C(O)H or —C(O)$R^6$;
  (d) —CO$_2R^6$;
  (e) —SH, —S(O)$_n R^6$, —S(O)$_m$—OH, —S(O)$_m$—O$R^6$, —O—S(O)$_n R^6$, —O—S(O)$_m$OH or —O—S(O)$_m$—O$R^6$;
  (f) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{10}$ is
  (a) hydrogen;
  (b) —C(O)H or —C(O)$R^6$, except when $Z^5$ is —C(O)— and $R^9$ is —C(O)H, —C(O)$R^6$ or —CO$_2R^6$; or
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{11}$ is
  (a) hydrogen;
  (b) hydroxyl;
  (c) —C(O)H, —C(O)$R^6$ or CO$_2R^6$; or
  (d) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

or any two of $R^9$, $R^{10}$ and $R^{11}$ together are alkylene or alkenylene (either of which may be substituted with $Z^1$, $Z^2$ and $Z^3$), completing a 3- to 8-membered saturated, unsaturated or aromatic ring together with the atoms to which they are attached;

$Z^1$, $Z^2$ and $Z^3$ are each independently
  (a) hydrogen;
  (b) halo;
  (c) hydroxy;
  (d) alkyl;
  (e) alkenyl;
  (f) aralkyl;
  (g) alkoxy;
  (h) aryloxy;
  (i) aralkoxy;
  (j) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
  (k) oxo;
  (l) nitro;
  (m) cyano;
  (n) —C(O)H or —C(O)Z$^6$;
  (o) —CO$_2$H or —CO$_2$Z$^6$;
  (p) —Z$^4$—NZ$^7$Z$^8$;
  (q) —Z$^4$—N(Z$^{11}$)—Z$^5$—Z$^6$; or
  (r) —Z$^4$—N(Z$^{11}$)—Z$^5$—NZ$^7$Z$^8$;

$Z^4$ and $Z^5$ are each independently
  (a) a single bond;
  (b) —Z$^9$—S(O)$_n$—Z$^{10}$—;
  (c) —Z$^9$—C(O)—Z$^{10}$—;
  (d) —Z$^9$—C(S)—Z$^{10}$—;
  (e) —Z$^9$—O—Z$^{10}$—;
  (f) —Z$^9$—S—Z$^{10}$—; or
  (g) —Z$^9$—O—C(O)—Z$^{10}$—;

$Z^6$, $Z^7$ and $Z^8$ are each independently hydrogen, alkyl, alkenyl, alkynyl, cycloalkyl, cycloalkylalkyl, cycloalkenyl, cycloalkenylalkyl, aryl or aralkyl, or $Z^7$ and $Z^8$ together are alkylene or alkenylene, completing a 3- to 8-membered saturated, unsaturated or aromatic ring together with the nitrogen atom to which they are attached;

$Z^9$ and $Z^{10}$ are each independently a single bond, alkylene, alkenylene or alkynylene;

$Z^{11}$ is
  (a) hydrogen;
  (b) hydroxyl;
  (c) —C(O)H, —C(O)Z$^6$ or —CO$_2$Z$^6$;
  (d) alkyl, alkenyl, alkynyl, alkoxy, cycloalkyl, cycloalkylalkyl, cycloalkenyl, cycloalkenylalkyl, aryl or aralkyl;

or any two of $Z^7$, $Z^8$ and $Z^{11}$ together are alkylene or alkenylene, completing a 3- to 8-membered saturated, unsaturated or aromatic ring together with the atoms to which they are attached;

m is 1 or 2; and
  n is 0, 1 or 2.

For coumpound I, it is preferred that:

$R^1$ is phenyl or phenoxy, optionally substituted with one or more alkyl, alkoxy, —NZ$^7$Z$^8$, halo and hydroxy;

$R^2$ and $R^3$ are each independently hydrogen, alkyl or —NR$^7$R$^8$;

$R^4$ and $R^5$ are alkyl; and $R^7$, $R^8$, $Z^7$ and $Z^8$ are each independently hydrogen, alkyl or —C(O)alkyl.

Most preferred compounds are those wherein:

$R^1$ is phenyl or phenoxy, optionally substituted with alkyl, alkoxy, amino, alkylamino, dialkylamino, alkanoylamino or hydroxy;

$R^2$ and $R^3$ are each independently hydrogen, alkyl of 1 to 4 carbon atoms, amino, alkylamino, dialkylamino or alkanoylamino; and $R^4$ and $R^5$ are alkyl of 1 to 4 carbon atoms, especially methyl.

DETAILED DESCRIPTION OF THE INVENTION

Listed below are definitions of terms used in this specification. These definitions apply to the terms as used throughout this specification, individually or as part of another group, unless otherwise limited in specific instances.

The terms "alkyl" and "alkoxy" refer to straight or branched chain hydrocarbon groups having 1 to 10 carbon atoms. The terms "lower alkyl" and "lower alkoxy" refer to groups of 1 to 4 carbon atoms, which are preferred.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH.

The term "alkynylene" refers to a straight chain bridge of 2 to 5 carbon atoms that has a triple bond therein, is connected by singe bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The term "alkanoyl" refers to groups of the formula —C(O)alkyl.

The terms "cycloalkyl" and "cycloalkenyl" refer to cyclic hydrocarbon groups of 3 to 8 carbon atoms.

The terms "halogen" and "halo" refer to fluorine, chlorine, bromine and iodine.

The compounds of formula I form salts which are also within the scope of this invention. Pharmaceutically acceptable (i.e., non-toxic, physiologically acceptable) salts are preferred, although other salts are also useful, e.g, in isolating or purifying the compounds of this invention.

The compounds of formula I may form salts with alkali metals such as sodium, potassium and lithium, with alkaline earth metals such as calcium and magnesium, with organic bases such as dicyclohexylamine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^5$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate, and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^5$ substituents comprise a basic moiety such as amino, zwitterions ("inner salts") may be formed.

Certain of the $R^1$ to $R^5$ substituents of compound I may contain asymmetric carbon atoms. Such compounds of formula I may exist, therefore, in enantiomeric and diastereomeric forms and in racemic mixtures thereof. All are within the scope of this invention. When $R^1$ is aryl, compound I may exist as enantiomers even in the absence of asymmetric carbons. All such enantiomers are also within the scope of this invention. When $R^1$ is aryl and additionally there are asymmetric carbons present, compounds of formula I may exist in diastereomeric forms and in racemic mixtures thereof. All these are within the scope of the invention as well.

The compounds of formula I are antagonists of ET-1, ET-2 and/or ET-3 and are useful in treatment of all endothelin-dependent disorders. They are thus useful as antihypertensive agents. By the administration of a composition having one (or a combination) of the compounds of this invention, the blood pressure of a hypertensive mammalian (e.g., human) host is reduced.

The compounds of the present invention are also useful in the treatment of disorders related to renal, glomerular and mesangial cell function, including chronic renal failure, glomerular injury, renal damage secondary to old age, nephrosclerosis (especially hypertensive nephrosclerosis), nephrotoxicity (including nephrotoxicity related to imaging and contrast agents), and the like. The compounds of this invention may also be useful in the treatment of disorders related to paracrine and endocrine function.

The compounds of the present invention are also useful in the treatment of endotoxemia or endotoxin shock.

The compounds of the present invention are also useful as anti-ischemic agents for the treatment of, for example, heart, renal and cerebral ischemia, coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease); treatment of cardiac hypertrophy (e.g., hypertrophic cardiomyopathy); treatment of pulmonary hypertension; treatment of central nervous system vascular disorders, such as stroke, migraine and subarachnoid hemorrhage; treatment of central nervous system behavioral disorders; treatment of gastrointestinal diseases such as ulcerative colitis and Crohn's disease; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatoxicity and sudden death.

The compounds of this invention can also be formulated in combination with endothelin converting enzyme (ECE) inhibitors, such as phosphoramidon; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and saltsof such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomenular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

An amine

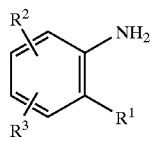

II is treated with an acid (e.g., hydrochloric acid) and sodium nitrite in a solvent (e.g., water, acetic acid) at about −20 to 0° C., followed by sulfur dioxide, and a copper (I) salt (e.g., copper (I) chloride) in a solvent (e.g., acetic acid) at about 5 to 30° C. to form a sulfonyl halide

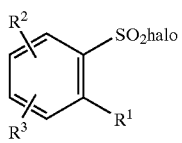

III

When $R^1$ is halogen and one of $R^2$ or $R^3$ is alkoxy or aralkoxy, the sulfonyl halide of the formula III can also be prepared by alkylating, in the presence of a base, the hydroxy group of a hydroxy benzene sulfonate, halogenating the ring, and then treating with a halogenating agent (e.g, $PCl_5$). Sulfonyl halide III is then coupled with an isoxazolamine

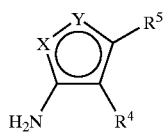

IV in an anhydrous organic solvent (e.g., pyridine) to form compound I.

Compound I wherein $R^1$, $R^2$ or $R^3$ is aryl may be prepared by metal (e.g., palladium (0)) catalyzed coupling of the associated halo compound I (wherein $R^1$, $R^2$ or $R^3$ is halogen) with aryl metalloids (i.e., aryl derivatives of tin, silicon, boron and the like, such as phenylboronic acid). See, for example, the procedures of Example 4. The phenylboronic acid may be prepared by treating an aryl halide with n-butyllithium or magnesium turnings in tetrahydrofuran, adding trimethylborate and finally adding aqueous hydrochloric acid. Alternatively, a phenylboronic acid may be prepared by adding a phenyl magnesium bromide to a solution of trimethyl borate and quenching with aqueous hydrochloric acid. Depending on the desired result, certain phenylboronic acids may be prepared by mixing an aryldihalide with palladium (0) and adding a grignard reagent to prepare a desired aryl halide before treating the aryl halide as described above.

Also depending on the desired result, certain phenylboronic acids may be prepared by ortho lithiation of a substituted benzene. Treatment of the substituted benzene with, for example, n-butyl lithium removes an ortho proton. Subsequent treatment with $B(OCH_3)_3$ and HCl results in an ortho-substituted phenylboronic acid. When the substituted benzene is an alkyl substituted benzene, it can be prepared, for example, by metal (e.g., palladium (0)) catalyzed coupling of a halobenzene with an alkylborane.

Certain compounds of the formula I wherein $R^1$, $R^2$ or $R^3$ is aryl substituted with alkyl or cycloalkylalkyl can be similarly prepared with alkyl- or cycloalkylalkyl-phenylboronic acids. The alkyl- or cycloalkylalkyl-phenylboronic acids are prepared from the corresponding alkyl- or cycloalkylalkyl-substituted bromobenzene. These substituted bromobenzenes, in turn, can be prepared by treating substituted bromobenzaldehydes with a grignard reagent followed by elimination and hydrogenation, or with a Wittig reagent followed by hydrogenation.

There are several other alternatives for preparing a compound of the formula I wherein specifically $R^1$ is aryl. For example, a compound of the formula I may be prepared by metal (e.g., palladium (0)) catalyzed coupling of a halobenzenesulfonamide with a phenylboronic acid. The resulting biphenyl sulfonamide is reacted with a haloisoxazole and a base (e.g., $Cs_2CO_3$).

Alternatively, a halobenzene sulfonyl chloride may be reacted with a pyrrole. The product is coupled, using a metal (e.g., palladium(0)) catalyst, with a substituted phenylboronic acid, treated with a base (e.g., NaOH) and then $PCl_5$, and finally treated with an isoxazolamine of the formula IV.

Certain compounds of formula I in which one or more of $R^1$ to $R^3$ is alkylphenyl may be prepared by halogenation of the alkyl group of the appropriate alkyl phenyl group and displacement of the halogen with, for example, a cuprate reagent.

Compounds of the formula I may also be prepared by treating a halobenzene, substituted in the meta position, with $ClSO_3H$. The resulting substituted halobenzene sulfonyl chloride is then treated as described above.

For compounds wherein any of $R^1$ to $R^5$ comprise reactive functionalities, the reactants may be treated with protecting agents prior to coupling. The amine portion of the sulfonamide core may also need to be protected when different $R^1$, $R^2$ and $R^3$ groups are added. Suitable protecting agents and procedures for use thereof are generally known in the art. Exemplary protecting groups are benzyl, halocarbobenzyloxy, tosyl, methyl and the like for hydroxyl; and carbobenzyloxy, halocarbobenzyloxy, t-butoxy carbonyl, acetyl, benzoyl, methoxyethoxymethyl and the like for amino. The sulfonamide nitrogen may be protected with methoxyethoxymethyl, trimethylsilylethoxymethyl, t-butyl and the like. Protecting groups may be removed from the resulting protected analogues of compound I by treatment with one or more deprotecting agents. Suitable deprotecting agents and procedures for use thereof are generally known in the art.

To form compound I wherein one or more of $R^1$ to $R^3$ is —$NR^7R^8$, or $R^1$ is phenyl-$NR^7R^8$, and $R^7$ and/or $R^8$ is —$C(O)R^6$, the associated nonacyl sulfonic acid

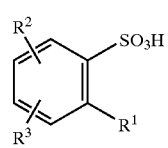

V is treated with water and an alkali metal hydroxide (e.g., sodium hydroxide) to form a sulfonic acid salt

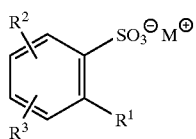

wherein M⁺ a lithium, sodium or potassium ion. Salt VI is treated with an acylating agent (e.g., acetic anhydride) at about 90 to 110° C. in either the acylating agent as solvent or in an anhydrous organic solvent (e.g., pyridine) to form the associated acylamine of formula VI, wherein one or more of $R^1$, $R^2$ and $R^3$ is —NR$^7R^8$, or $R^1$ is phenyl-NR$^7R^8$, and at least one of $R^7$ and $R^8$ is —C(O)R$^6$. Acylamine VI is then treated with a halosulfonic acid solution (e.g., chlorosulfonic acid) or with another halogenating agent (e.g., phosphorus pentachloride, thionyl chloride) at about 0° C. to 80° C. to form an acyl-sulfonyl halide III, which is coupled with isoxazolamine IV as described above to form compound I wherein at least one of $R^1$, $R^2$ and $R^3$ is —NR$^7R^8$, or $R^1$ is phenyl-NR$^7R^8$, and at least one of $R^7$ and $R^8$ is —C(O)R$^6$.

To form a compound of formula I wherein one or more of $R^1$ to $R^3$ is an aldehyde or acid, or $R^1$ is phenyl substituted with an aldehyde or acid, the corresponding hydroxyalkyl substituted benzene is oxidized.

To form a compound of formula I wherein one or more of $R^1$ to $R^3$ is alkoxy, the associated sulfonic acid V wherein one or more of $R^1$ to $R^3$ is hydroxy may be treated with an alkylating agent (e.g., dimethylsulfate) and an alkali metal hydroxide (e.g., sodium hydroxide) in an aqueous/organic solvent mixture (e.g., water/ethanol). The resulting alkoxy sulfonic acid salt VI may be used as described above to form coumpound I.

Certain compounds of formula I in which one or more of $R^1$ to $R^3$ is aryloxy may be prepared by displacement of the corresponding arylhalide with a metal salt of a phenol.

Monoamines of formula I (for example having —NR$^7R^8$ wherein one of $R^7$ and $R^8$ is hydrogen) are prepared from the associated free amine (for example wherein $R^7$ and $R^8$ are both hydrogen). The free amine is treated with (1) a ketone or aldehyde (e.g., acetone), (2) a reducing agent (e.g., sodium cyanoborohydride) or hydrogen gas ($H_2$) and a catalyst (e.g., palladium on carbon), and (3) an acid (e.g., acetic acid, hydrochloric acid) in an organic solvent (e.g., methanol) to form the associated monoamine coumpound I. Diamines of formula I, of course, may be similarly prepared. Additionally, the monoamines may be acylated or treated with isocyanates to form ureas.

Monoamines of formula I (for example having —NR$^7R^8$ wherein one of $R^7$ and $R^8$ is hydrogen) may also be prepared from the associated acylamine by treatment with a reducing agent, for example, borane.

The invention will now be further described by the following working examples, which are preferred embodiments of the invention. These examples are meant to be illustrative rather than limiting.

EXAMPLE 1

N-(3,4-Dimethyl-5-isoxazolyl)[1,1'-biphenyl]-2-sulfonamide

A. 2-Phenylbenzenesulfonyl Chloride

2-Aminobiphenyl (5.08 g, 30 mmol) was added in one portion to a mixture of concentrated hydrochloric acid (10 mL) and glacial acetic acid (3 mL) in a beaker equipped with a mechanical stirrer. The thick pink hydrochloride salt was cooled in a dry ice-ethanol bath to −10° C. A solution of sodium nitrite (2.24 g, 32.5 mmol) in water (3.5 mL) was added dropwise at a rate such that the temperature did not exceed −5° C. This mixture was stirred for 45 min maintaining the temperature between −10° C. and −5° C. In a separate beaker, sulfur dioxide gas was bubbled through 30 mL of glacial acetic acid under vigorous stirring for 20 minutes. Copper(I) chloride (0.75 g) was added to this solution and bubbling of sulfur dioxide gas was continued until the yellow-green suspension became blue-green and most of the solids dissolved (about 30 minutes). This mixture was cooled to 10° C. in an ice bath with stirring and to it was added the diazotization mixture in portions over 30 minutes, after which period the ice-bath was removed and the mixture was allowed to warm to room temperature. The green mixture was stirred for an additional 30 minutes and poured into ice-water (100 mL, 1:1) and the precipitated gummy solid was extracted with ether (3×75 mL). The combined extracts were washed with saturated sodium bicarbonate solution until neutral and washed with water (2×50 mL), dried (magnesium sulfate) and concentrated under vacuum to yield 5.0 g (66%) of compound A as a light brown solid.

B. N-(3,4-Dimethyl-5-isoxazolyl)[1,1'-biphenyl]-2-sulfonamide

To a solution of 3,4-dimethyl-5-isoxazolamine (1.32 g, 11.8 mmol) in dry pyridine (5 mL) was added compound A (2.5 g, 9.8 mmol) in portions over 15 minutes. More pyridine was added to bring the total volume to approximately 10 mL. The resulting dark red-brown solution was stirred overnight at room temperature. The reaction mixture was added dropwise to ice-water (100 mL, 1:1) and the resulting tarry precipitate was filtered through Celite®, and the filtrate was acidified with 6 N hydrochloric acid to pH 2. A brown solid was filtered, washed with water and dried. This solid (1.4 g) was purified by flash chromatography over silica gel with ethyl acetate:hexanes (1:1) to give 1.1 g (34%) of Example 1 as a yellow solid.

Melting point: 171–173° C.; Analysis for $C_{17}H_{16}N_2O_3S$ (328.4); Calc'd: C, 62.18; H, 4.91; N, 8.53; S, 9.76. Found: C, 62.27; H, 4.92; N, 8.39; S, 10.02.

EXAMPLE 2

N-(3,4-Dimethyl-5-isoxazolyl)-2-bromobenzenesulfonamide

To a solution of 3.0 g (11.74 mmol) of 2-bromobenzenesulfonyl chloride in 10 mL of pyridine was added 1.32 g (11.74 mmol) of 3,4-dimethyl-5-isoxazolamine. The mixture was stirred at room temperature under argon overnight, added to 150 mL of ice water and filtered. The filtrate was acidified to pH 2 using 6 N aqueous hydrochloric acid and the grey solid was filtered and dried. The solid was crystallized from methanol/water to afford 4.0 g (greater than 100%) of Example 2 as tan crystalline needles.

Melting point: 125–126° C.; Analysis for $C_{11}H_{11}BrN_2O_3S$; Calc'd: C, 39.89; H, 3.35; N, 8.46; S, 9.68; Br, 24.13. Found: C, 39.32; H, 3.35; N, 8.21; S, 9.52; Br, 24.08.

EXAMPLE 3

N-(3,4-Dimethyl-5-isoxazolyl)-2-phenoxybenzenesulfonamide

A. 2-Phenoxybenzenesulfonyl Chloride p To a solution of 6.0 g (32.4 mmol) of 2-phenoxyaniline in 15 mL of concentrated hydrochloric acid and 5 mL of glacial acetic acid at −5° C. was added a solution of sodium nitrite (2.35 g, 34 mmol) in 5 mL of water dropwise over 15 minutes. The solution was stirred at −5° C. for an additional 1 hour. During the diazotization, sulfur dioxide was bubbled through 30 mL of glacial acetic acid until it was saturated (about 10 minutes). Cuprous chloride (1.5 g) was then added and the introduction of sulfur dioxide was continued (about 20 minutes) until the yellow-green suspension became bluegreen. The mixture was cooled to 10° C. and the solution containing the diazonium salt was added in portions over 15 minutes. The green reaction mixture was warmed to room temperature and stirred for an additional 1 hour. Water (150 mL) was added and the solution was extracted with ether (3×100 mL). The combined ether extracts were repeatedly washed with 5% aqueous sodium hydrogen carbonate (5×150 mL) until neutral and then with water (150 mL) and dried and evaporated to give 2.75 g of compound A as a brown syrup.

B. N-(3,4-Dimethyl-5-isoxazolyl)-2-phenoxybenzenesulfonamide

To a solution of 2.7 g of crude compound A (10 mmol) in 15 mL of pyridine was added 0.79 g (7 mmol) of 3,4-dimethyl-5-isoxazolamine, and the solution was stirred at room temperature overnight. The solution was diluted with 150 mL of ice water and the residual gum (2.5 g) was filtered. The filtrate was acidified to pH 2 using 6 N aqueous hydrochloric acid and the solid was filtered (0.23 g) and chromatographed on 10 g of silica using 1:1 hexanes/ethyl acetate to provide 0.16 g (7%) of Example 3 as a white crystalline solid.

Melting point: 181–182° C.; Analysis for $C_{17}H_{16}N_2O_4S$; Calc'd: C, 59.29; H, 4.68; N, 8.13; S, 9.31. Found: C, 59.15; H, 4.57; N, 8.08; S, 9.35.

EXAMPLE 4

3'-Amino-N-(3,4-dimethyl-5-isoxazolyl)[1,1'-biphenyl]-2-sulfonamide

A. 2-Bromo-N-(3,4-dimethyl-5-isoxazolyl)-N'-(methoxyethoxymethyl)benzenesulfonamide To a solution of 1.1 g (3.33 mmol) of 2-bromo-N-(3,4-dimethyl-5-isoxazolyl)benzenesulfonamide (Example 2) in 15 mL of tetrahydrofuran at room temperature under argon was added 0.19 g (4.8 mmol) of sodium hydride (60% suspension in mineral oil) in portions, and the solution was stirred at room temperature for 10 minutes. Methoxyethoxymethyl chloride (0.55 g, 4.4 mmol) was then added and the solution was stirred overnight. The mixture was concentrated and diluted with 30 mL of water and extracted with 3×40 mL of ethyl acetate. The combined organic extracts were washed with 50 mL of brine, dried and evaporated to provide 1.2 g (87%) of compound A as a brown gum.

B. 3'-Amino-N-(3,4-dimethyl-5-isoxazolyl)-N'-(methoxyethoxymethyl)[1,1'-biphenyl]-2-sulfonamide To a solution of 1.12 g (2.67 mmol) of compound A and 0.15 g (0.13 mmol) of tetrakis(triphenylphosphine)palladium(0) in 15 mL of benzene under argon, 7.6 mL of 2 M aqueous sodium carbonate was added, followed by 0.46 g (2.93 mmol) of 3-aminophenylboronic acid in 5 mL of 95% ethanol. The mixture was refluxed overnight, diluted with 35 mL of water, and extracted with 3×35 mL of ethyl acetate. The combined organic extracts were washed once with 35 mL of brine, dried and evaporated. The residue was chromatographed on 120 g of silica gel using hexanes/ethyl acetate (1:2) to afford 0.75 g (65%) of compound B as a gum.

C. 3'-Amino-N-(3,4-dimethyl-5-isoxazolyl)[1,1'-biphenyl]-2-sulfonamide

To a solution of 0.72 g (1.7 mmol) of compound B in 10 mL of 95% ethanol, 10 mL of 3 N aqueous hydrochloric acid was added and the solution was refluxed for 7 hours. The mixture was concentrated, diluted with 40 mL of water and neutralized to pH 7 using aqueous sodium hydrogen carbonate. The mixture was extracted with 4×50 mL of ethyl acetate and the combined organic extracts were washed once with 50 mL of brine, dried and evaporated. The residue was chromatographed on 25 g of silica using methylene chloride:methanol (97:3) and triturated with ether/hexanes to afford 86 mg of Example 4 as a tan solid.

Melting point: 157–160° C.; Analysis for $C_{17}H_{17}N_3O_3S \cdot 0.1C_6H_{14}$; Calc'd: C, 60.05; H, 5.27; N, 11.94; S, 9.11. Found: C, 59.83; H, 5.11; N, 11.55; S, 8.69.

EXAMPLE 5

2-Fluoro-N-(3,4-dimethyl-5-isoxazolyl)benzenesulfonamide

To a solution of 2.88 g (25.7 mmol) of 3,4-dimethyl-5-isoxazolamine in 15 mL of pyridine was added 5.0 g (25.7 mmol) of 2-fluorobenzenesulfonyl chloride. The mixture was stirred at room temperature overnight, poured into 100 mL of ice water and the resulting mixture was filtered. The filtrate was acidified to pH 2 using 6 N aqueous hydrochloric acid and the solid was filtered and dried to provide 3.2 g (46%) of Example 5 as a tan solid.

Melting point: 122–124° C.; Analysis for $C_{11}H_{11}FN_2O_3S$; Calc'd: C, 48.88; H, 4.10; N, 10.36; S, 11.86; F, 7.03. Found: C, 48.93; H, 3.77, N, 10.38; S, 12.10; F, 6.70.

EXAMPLE 6

N-[3-[[(3,4-Dimethyl-5-isoxazolyl)amino]sulfonyl]-4-methylphenyl]acetamide

A. 5-Amino-2-methylbenzenesulfonic Acid, Sodium Salt

To a suspension of 5-amino-2-methylbenzenesulfonic acid (25 g, 134 mmol) in water (100 mL) was added 4 N sodium hydroxide (34 mL). The resulting clear brown solution was evaporated and the remaining brown solid was washed several times with ether and dried to afford 31.3 g of compound A as a brown solid (greater than 100%).

B. 5-Acetylamino-2-methylbenzenesulfonic Acid, Sodium Salt

A suspension of crude compound A (25 g, about 107 mmol) in acetic anhydride (100 mL) was heated at 100° C. for 3 hours, allowed to stand overnight at room temperature and evaporated. The residual gummy brown solid was suspended in ether, the suspension was filtered and the solid was washed twice with ether to afford 32.3 g of compound B as a tan solid (greater than 100%), which appeared to be hygroscopic.

C. 5-Acetylamino-2-methylbenzenesulfonyl Chloride

A mixture of Compound B (18 g, about 71.6 mmol) and phosphorus pentachloride (30 g, 143 mmol) was heated at 75° C. with stirring for 2.25 hours, during which time the solids liquefied to a brown gum. The mixture was cooled and the dark brown semi-solid was poured into ice water (400 mL). The brown solid that formed was filtered, washed with water and dissolved in methylene chloride. The organic solution was washed with water and dried (magnesium sulfate) and evaporated to afford 14.4 g of brown foamy gum. This material was dissolved in methylene chloride and passed through a pad of silica using 50% ethyl acetate/hexanes to afford 10.2 g of brown gum. Flash chromatography on silica with 60% ethyl acetate/hexanes afforded 2.01 g of compound C (11%) as a light yellow oil that crystallized on standing.

D. N-[3-[[(3,4-Dimethyl-5-isoxazolyl)amino]-sulfonyl]-4-methylphenyl]acetamide

A solution of Compound C (1.02 g, 4.12 mmol), 3,4-dimethyl-5-isoxazolamine (0.55 g, 4.94 mmol) and dimethylaminopyridine (0.10 g, 0.82 mmol) in 4 mL of pyridine was heated at 70° C. for 2.25 hours, cooled and poured onto iced dilute hydrochloric acid. The resulting tan solid was filtered, rinsed with water and dissolved in 10% isopropanol/methylene chloride. The solution was dried (magnesium sulfate) and evaporated to afford 1.09 g of a brown foamy gum which was flash-chromatographed on silica (2%, then 3%, then 5%, then 10% methahol/methylene chloride) to provide 0.37 g of clean Example 6 as a white foam. There was also obtained 0.43 g of impure Example 6. Crystallization of the clean material from aqueous ethanol afforded 0.25 g of Example 6 (19%) as light tan crystals.

Melting point: 203–204° C.; Analysis for $C_{14}H_{17}N_3O_4S$; Calc'd: C, 52.00; H, 5.30; N, 12.99; S, 9.91. Found: C, 51.81; H, 5.31; N, 12.86; S, 9.94.

EXAMPLE 7

5-Amino-N-(3,4-Dimethyl-5-isoxazolyl)-2-methylbenzenesulfonamide

A solution of crude Example 6 (0.40 g, 1.24 mmol) in 4 N sodium hydroxide (4 mL, 16 mmol) and methanol (1 mL) was heated at 65° C. for 4.5 hours, cooled and the methanol evaporated. The residue was extracted with ether and the aqueous solution was acidified to pH 2.5 with concentrated hydrochloric acid and extracted twice with 10% isopropanol/methylene chloride. The organic phase was dried (magnesium sulfate) and evaporated to afford 0.37 g of a yellow oil that crystallized on standing. Recrystallization from aqueous ethanol afforded 0.24 g of Example 7 (69%) as light tan needles.

Melting point: 204–205° C.; Analysis for $C_{12}H_{15}N_3O_3S$; Calc'd: C, 51.23; H, 5.37; N, 14.94; S, 11.40. Found: C, 51.52; H, 5.37; N, 14.92; S, 11.57.

EXAMPLE 8

N-(3,4-Dimethyl-5-isoxazolyl)-2-(1-methylethyl)-benzenesulfonamide

A. 2-Isopropylbenzenesulfonate, Sodium Salt

To a solution of 30% hydrogen peroxide (10 mL) in glacial acetic acid (10 mL) at 50° C. was added a solution of 2-isopropylthiophenol (1 g, 6.58 mmol) in 5 mL of glacial acetic acid over 1 hour. After the addition was completed, the reaction was heated to 60° C. for 1 hour. The reaction was concentrated in vacuo and the residue was lyophilized from water to afford 1.3 g of a white solid. The solid (theoretically 6.5 mmol) was dissolved in 5 mL of water and 4 N aqueous sodium hydroxide (1.62 mL, 6.5 mmol) was added. The solution was lyophilized to afford 1.4 g (100%) of compound A as a white solid.

MS $(M+NH_4)^+$ 218; $(M-H)^-$ 199.

B. 2-Isopropylbenzenesulfonyl Chloride

To a slurry of compound A (600 mg, 2.50 mmol) in chloroform (20 mL) was added chlorosulfonic acid (0.33 mL, 5.0 mmol) dropwise to maintain the reaction temperature below 50° C. The reaction was heated to 60° C. overnight, cooled to room temperature and poured into ice-water. The aqueous solution was extracted with chloroform (three times). The combined organic phases were dried over sodium sulfate. The solvent was removed in vacuo to afford 410 mg (74.5%) of compound B.

C. N-(3,4-Dimethyl-5-isoxazolyl)-2-(1-methylethyl)-benzenesulfonamide

A solution of compound B (410 mg, 1.88 mmol), dimethylaminopyridine (60 mg, 0.49 mmol), and 3,4-dimethyl-5-isoxazolamine (230 mg, 2.06 mmol) in pyridine (8 mL) was heated in an oil bath at 70° C. for 2 hours. The reaction was poured onto iced 10% hydrochloric acid. The mixture was extracted with ethyl acetate (three times) and the combined organic phases were extracted with 10% aqueous sodium hydrogen carbonate. The aqueous solution was acidified to pH 3 and extracted with ethyl acetate (three times). The combined organic phases were washed with saturated sodium chloride, dried over sodium sulfate and evaporated. The residue was applied to a silica gel column (20×130 mm) and eluted with ethyl acetate:hexanes (1:1). The enriched product fractions were combined and evaporated. The residue was applied to three 20×20 chromatographic thick plates. The plates were eluted with 1:1 ether::hexanes. The desired bands were cut and extracted with ethyl acetate. The silica gel was filtered and the organic solvent was evaporated to afford 192.2 mg (35%) of Example 8 as a yellow semi-solid.

MS: $(M+H)^+$ 295. Analysis for $C_{14}H_{18}N_2O_3S \cdot 0.58H_2O$; Calc'd: C, 55.15; H, 6.34; N, 9.19; S, 10.52. Found: C, 55.22; H, 6.42; N, 9.12; S, 10.72.

EXAMPLE 9

N-(3,4-Dimethyl-5-isoxazolyl)-2-nitro-benzenesulfonamide

To a solution of 4.04 g (36 mmol) of 3,4-dimethyl-5-isoxazolamine in 15 mL of pyridine, 8.0 g (36 mmol) of 2-nitrobenzenesulfonyl chloride was added and the solution was stirred at room temperature overnight. The mixture was poured into 100 mL of ice water and filtered. The filtrate was acidified to pH 2 using 6 N aqueous hydrochloric acid and the mixture was extracted with 4×125 mL of ethyl acetate. The combined organic extracts were washed with 75 mL of brine, dried and evaporated to provide 9.1 g of a dark brown residue. This material was chromatographed on silica gel using hexanes/ethyl acetate (2:1) to provide 0.5 g of Example 9 as a light yellow solid.

Melting point: 91–94° C.; Analysis for $C_{11}H_{11}N_3O_5S$; Calc'd: C, 44.44; H, 3.73; N, 14.13; S, 10.78. Found: C, 44.75; H, 3.69, N, 14.01; S, 11.06.

EXAMPLE 10

2-Amino-N-(3,4-dimethyl-5-isoxazolyl) benzenesulfonamide

To a suspension of 135 mg of 10% palladium on carbon in 20 mL of methanol under argon, 0.9 g (3.03 mmol) of N-(3,4-dimethyl-5-isoxazolyl)-2-nitrobenzenesulfonamide (Example 9) in 20 mL of methanol was added. The solution was hydrogenated with a balloon filled with hydrogen for 90 minutes. The mixture was filtered through Celite® and the filtrate was concentrated to afford 0.9 g of a gum. This material was chromatographed on silica initially with 9:1 methylene chloride:methanol and then with 1:1 hexanes:ethyl acetate to provide 0.2 g (24%) of Example 10 as a white solid.

Melting point: 116–118° C.; Analysis for $C_{11}H_{13}N_3O_3S$; Calc'd: C, 49.43; H, 4.90; N, 15.72; S, 11.99. Found: C, 49.56; H, 4.80; N, 15.62; S, 11.89.

EXAMPLE 11

N-(3,4-Dimethyl-5-isoxazolyl)-4'-methyl[1,1'-biphenyl]-2-sulfonamide

A. 4'-Methyl-N-(3,4-dimethyl-5-isoxazolyl)-N-(methoxyethoxymethyl)[1,1'-biphenyl]-2-sulfonamide To a solution of 0.78 g (1.86 mmol) of compound A from Example 4 and 0.096 g (0.08 mmol) of tetrakis(triphenylphosphine)palladium(0) in 15 mL of benzene under argon, 8.0 mL of 2 M aqueous sodium carbonate was added followed by 0.38 g (2.79 mmol) of 4-methylphenylboronic acid in 10 mL of 95% ethanol. The mixture was refluxed overnight and diluted with 50 mL of water and extracted with 3×100 mL of ethyl acetate. The combined organic extracts were washed once with 100 mL of brine and dried and evaporated. The residue was chromatographed on 100 g of silica gel using hexanes/ethyl acetate (2:1) to afford 0.65 g (81%) of compound A as a colorless gum.

B. N-(3,4-Dimethyl-5-isoxazolyl)-4'-methyl[1,1'-biphenyl]-2-sulfonamide

To a solution of 0.56 g (1.3 mmol) of compound A in 10 mL of 95% ethanol, 10 mL of 3 N aqueous hydrochloric acid was added and the solution was refluxed for 18 hours. The mixture was concentrated and diluted with 25 mL of water. The mixture was extracted with 3×50 mL of ethyl acetate and the combined organic extracts were washed once with 50 mL of brine and dried and evaporated. Crystallization of the residue (0.41 g) from hexanes/ethyl acetate provided 0.37 g (83%) of Example 11 in two crops.

Melting point: 126–127° C.; Analysis for $C_{18}H_{18}N_2O_3S$; Calc'd: C, 63.14; H, 5.30; N, 8.18; S, 9.36. Found: C, 63.03; H, 5.29; N, 8.07; S, 9.34.

EXAMPLE 12

2'-Amino-N-(3,4-dimethyl-5-isoxazolyl)-[1,1'-biphenyl]-2-sulfonamide

A. 2'-Amino-N-(3,4-dimethyl-5-isoxazolyl)-N-[(2-methoxyethoxy)methyl][1,1'-biphenyl]-2-sulfonamide To a solution of compound A from Example 4 (0.5 g, 1.19 mmol) and tetrakis(triphenylphosphine)palladium(0) (0.062 g, 0.05 mmol) in 10 mL of benzene under argon, 4.0 mL of 2M aqueous sodium carbonate was added followed by 2-amino-phenylboronic acid (0.245 g, 1.79 mmol) in 5 mL of 95% ethanol. The mixture was refluxed for 10 hours, diluted with 50 mL of water and extracted with ethyl acetate (3×50 mL). The combined organic extracts were washed once with 50 mL of brine, dried and evaporated. The residue was chromatographed on 75 g of silica gel using hexanes/ethyl acetate (2:1) to afford 0.39 g (76%) of compound A as a colorless gum.

B. 2'-Amino-N-(3,4-dimethyl-5-isoxazolyl)-[1,1'-biphenyl]-2-sulfonamide

To a solution of compound A (0.35 g, 0.81 mmol) in 10 mL of 95% ethanol, 10 mL of 3N aqueous hydrochloric acid was added and the solution was refluxed for 6 hours. The mixture was concentrated, diluted with 10 mL of water, neutralized with saturated aqueous sodium hydrogen carbonate and acidified to pH 4 using glacial acetic acid. The mixture was extracted with ethyl acetate (3×25 mL) and the combined organic extracts were washed once with 50 mL of brine, dried and evaporated. Chromatography of the residue on 50 g silica gel using hexanes/ethyl acetate (1:1) provided 0.087 g of a gum. Repeated crystallizations from ethyl acetate:methanol:hexanes (1:1:20) afforded Example 12 as a light brown solid, m.p. 182–183° C.

Analysis for $C_{17}H_{17}N_3O_3S$; Calc'd: C, 59.46; H, 4.99; N, 12.24; S, 9.34. Found: C, 59.17; H, 5.04; N, 11.87; S, 9.73.

EXAMPLE 13

3'-(Dimethylamino)-N-(3,4-dimethyl-5-isoxazolyl)[1,1'-biphenyl]-2-sulfonamide

To a solution of Example 4 (0.46 g, 1.34 mmol) in methanol (15 mL), 37% aqueous formaldehyde (0.44 mL, 5.36 mmol) and glacial acetic acid (0.49 g) were added with stirring. Sodium cyanoborohydride (0.34 g, 5.36 mmol) was added over 10 minutes and the solution was stirred overnight. The mixture was concentrated to about 10 mL, diluted with water (40 ml) and extracted with ethyl acetate (3×35 mL). The combined organic extracts were washed with brine (50 mL), dried (magnesium sulfate) and evaporated. The gum (0.45 g) thus obtained was chromatographed on 100 g of silica gel using hexanes/ethyl acetate (3:1) to afford 0.21 g (42%) of Example 13 as an off-white solid, m.p. 67–70° C.

Analysis for $C_{19}H_{21}N_3O_3S \cdot 0.25\ H_2O$; Calc'd: C, 60.69; H, 5.76; N, 11.18; S, 8.53. Found: C, 60.92; H, 5.74; N, 10.95; S, 8.33.

EXAMPLE 14

N-(3,4-Dimethyl-5-isoxazolyl)-2-(trifluoromethyl)benzenesulfonamide

To a solution of 1.38 g (12.26 mmol) of 3,4-dimethyl-5-isoxazolamine in 10 mL of pyridine, 3.0 g (12.26 mmol) of 2-trifluoromethylbenzenesulfonyl chloride was added and the solution was stirred at room temperature under argon overnight. The mixture was added to 100 mL of ice water and filtered. The filtrate was acidified to pH 2 using 6N aqueous hydrochloric acid and the resultant gum was filtered and chromatographed on silica gel (200 g) using 3% methanol in methylene chloride to provide a colorless gum. This material was crystallized from hexanes/ethyl acetate to afford 2.0 g (51%) of Example 14 as white crystalline needles, m.p. 99–100° C.

Analysis for $C_{12}H_{11}F_3N_2O_3S$; Calc'd: C, 45.00; H, 3.46; $N_{8.75}$; S, 10.01; F, 17.80. Found: C, 44.67; H, 3.55; N, 8.74; S, 10.51; F, 18.19.

EXAMPLE 15

2-Chloro-N-(3,4-dimethyl-5-isoxazolyl)-6-methylbenzenesulfonamide

Example 15 was prepared from 3,4-dimethyl-5-isoxazolamine and 2-chloro-6-methylbenzenesulfonyl chloride as described for Example 14. Crystallization from methanol/water afforded Example 15 as white crystalline prisms, m.p. 181–182° C.

Analysis for $C_{12}H_{13}ClN_2O_3S$; Calc'd: C, 47.92; H, 4.36; N, 9.31; S, 10.66; Cl, 10.66. Found: C, 47.61; H, 4.25; N, 9.07; S, 10.67; Cl, 10.67.

EXAMPLE 16

4'-(Dimethylamino)-N-(3,4-dimethyl-5-isoxazolyl)[1,1'-biphenyl]-2-sulfonamide

A. 4'-(Dimethylamino)-N-(3,4-dimethyl-5-isoxazolyl)-N-[(2-methoxyethoxy)methyl][1,1'-biphenyl]-2-sulfonamide Compound A was prepared from 4-dimethylaminophenylboronic acid and compound A from Example 4 as described for compound A from Example 12. Chromatography on silica gel using 3:1 hexanes/ethyl acetate afforded compound A as a colorless gum.

B. 4'-(Dimethylamino)-N-(3,4-dimethyl-5-isoxazolyl)[1,1'-biphenyl]-2-sulfonamide Example 16 was prepared from compound A as described for Example 12, with refluxing for 8 hours. Before ethyl acetate extraction, the aqueous phase was taken to pH 6 using glacial acetic acid. Chromatography on silica gel using 2:1 hexanes/methylene chloride and crystallization from hexanes/ethyl acetate provided Example 16 as colorless prisms, m.p. 135–136° C.

Analysis for $C_{19}H_{21}N_3O_3S$; Calc'd: C, 61.44; H, 5.70; N, 11.31; S, 8.63. Found: C, 61.26; H, 5.55; N, 11.15; S, 8.99.

EXAMPLE 17

N-[2'-[[(3,4-Dimethyl-5-isoxazolyl)amino]sulfonyl] [1,1'-biphenyl]-3-yl]acetamide To a solution of Example 4 (0.3 g, 0.87 mmol) in pyridine (5 mL), acetic anhydride (0.13 g) was added and the mixture was stirred at room temperature overnight. The mixture was concentrated and diluted with water (30 mL) and extracted with ethyl acetate (3×25 mL). The combined organic extracts were washed with brine (30 mL), dried (magnesium sulfate) and evaporated. The white solid (0.31 g) thus obtained was chromatographed on 75 g of silica gel using hexanes/ethyl acetate (2:1) to afford 0.18 g (54%) of Example 17 as a white solid, m.p. 168–171° C.

Analysis for $C_{19}H_{19}N_3O_4S$; Calc'd: C, 59.21; H, 4.97; N, 10.90; S, 8.32. Found: C, 59.33; H, 4.86; N, 10.57; S, 8.47.

EXAMPLE 18

N-(3,4-Dimethyl-5-isoxazolyl)-4'-propyl[1,1'-biphenyl]-2-sulfonamide

A. 4-Propylphenylboronic Acid

To a solution of trimethylborate (2.6 g, 25 mmol) in 10 mL of ether at −78° C. under argon, 4-propylphenyl magnesium bromide (1.7 M solution in ether, 14.7 mL, 25 mmol) was added over 15 min. After 30 min at −78° C., the solution was warmed to room temperature and stirred for 90 min. The reaction was quenched by the addition of 10% aqueous hydrochloric acid (75 mL) and after 10 min the solution was extracted with ether (3×100 mL). The combined ether extracts were extracted with 1 M sodium hydroxide (2×100 mL) and the aqueous extracts were acidified with dilute hydrochloric acid to pH 2 and extracted with ether (2×100 mL). The combined ether extracts were washed once with water (100 mL), dried and evaporated to afford 1.85 g (45%) of compound A as a tan solid, m.p. 95–96° C.

B. N-(3,4-Dimethyl-5-isoxazolyl)-N-[(2-methoxyethoxy) methyl]-4'-propyl[1,1'-biphenyl]-2-sulfonamide Compound B was prepared from compound A and compound A from Example 4 as described for compound A from Example 12. Chromatography on silica gel using hexanes/ethyl acetate (3:1) afforded compound B as a colorless gum.

C. N-(3,4-Dimethyl-5-isoxazolyl)-4'-propyl[1,1'-biphenyl]-2-sulfonamide

To a solution of 0.70 g (1.53 mmol) of compound B in 15 mL of 95% ethanol, 15 mL of 3N aqueous hydrochloric acid was added. The solution was refluxed for 11 hours, concentrated and diluted with 25 mL of water. The mixture was extracted with ethyl acetate (3×50 mL) and the combined organic extracts were washed once with 50 mL of brine, dried and evaporated. Chromatography on 100 g of silica gel using 4:1 followed by 3:1 hexanes/ethyl acetate (1 L) provided 0.38 g (67%) of Example 18 as a colorless gum.

Analysis for $C_{20}H_{22}N_2O_3S$; Calc'd: C, 64.84; H, 5.99; N, 7.56; S, 8.65. Found: C, 64.52; H, 5.98; N, 7.26; S, 8.30.

EXAMPLE 19

2-(Dimethylamino)-N-(3,4-dimethyl-5-isoxazolyl) benzenesulfonamide

Example 19 was prepared from Example 10 as described for Example 13. Chromatography on silica gel using hexanes/ethyl acetate (4:1) afforded Example 19 as a colorless gum.

Analysis for $C_{13}H_{17}N_3O_3S$; Calc'd: C, 52.87; H, 5.80; N, 14.23; S, 10.85. Found: C, 52.99; H, 5.87; N, 14.06; S, 11.28.

EXAMPLE 20

2'-(Dimethylamino)-N-(3,4-dimethyl-5-isoxazolyl)-[1,1'-biphenyl]-2-sulfonamide

A. 2'-(Dimethylamino)-N-(3,4-dimethyl-5-isoxazolyl)-N-[(2-methoxyethoxy-methyl)[1,1'-biphenyl]-2-sulfonamide To a solution of compound A from Example 12 (0.45 g, 1.04 mmol) in 15 mL of methanol under argon, glacial acetic acid (1 mL) and 37% aqueous formaldehyde (0.25 mL, 3.13 mmol) were added. The solution was stirred for 15 minutes, sodium cyanoborohydride (0.20 g, 3.13 mmol) in 5 mL of methanol was added dropwise over 15 minutes and the solution was stirred for 24 hours. The mixture was evaporated, water (25 mL) was added and the mixture was extracted with ethyl acetate (2×50 mL). The combined organic extracts were dried and evaporated to provide 0.39 g (81%) of compound A as a light brown gum which solidified on standing.

B. 2'-(Dimethylamino)-N-(3,4-dimethyl-5-isoxazolyl)-[1,1'-biphenyl]-2-sulfonamide Example 20 was prepared from compound A as described for Example 12. Following chromatography on silica gel using 3:1 hexanes:ethyl acetate, crystallization from methylene chloride/hexanes (~1:5) afforded Example 20 as colorless prisms, m.p. 148–150° C.

Analysis for $C_{19}H_{21}N_3O_3S$; Calc'd: C, 61.44; H, 5.70; N, 11.31; S, 8.63. Found: C, 61.32; H, 5.69; N, 11.30; S, 8.72.

EXAMPLE 21

N-(3,4-Dimethyl-5-isoxazolyl)-4'-(2-methylpropyl)-[1,1'-biphenyl]-2-sulfonamide

A. 4-Isobutyl-phenylboronic Acid

To a suspension of 0.68 g (28.15 mmol) of magnesium turnings in 50 mL of tetrahydrofuran under argon, a crystal of iodine was added and a solution of 4-bromo-isobutylbenzene (6.0 g, 28.15 mmol) in 25 mL of tetrahydrofuran was added at such a rate that a gentle reflux was maintained. The mixture was refluxed for an additional 1 hour, cooled to room temperature and added in portions over 15 min to a solution of trimethylborate (2.93 g, 28.15 mmol) in 50 mL of ether at −78° C. under argon. After 30 min at −78° C., the solution was warmed to room temperature, stirred for 90 minutes and 10% aqueous hydrochloric acid (100 mL) was added. After 10 minutes, the solution was extracted with ether (3×100 mL) and the combined ether extracts were extracted with 1 M sodium hydroxide (3×100 mL). The aqueous extracts were acidified with dilute hydrochloric acid to pH 2 and extracted with ether (3×100 mL). The combined ether extracts were washed once with water (100 mL), dried and evaporated to afford 3.5 g of a white solid. Crystallization from ether/hexanes provided 2.3 g (46%) of compound A as a white solid in two crops, m.p. 134–135° C.

B. N-(3,4-Dimethyl-5-isoxazolyl)-N-[(2-methoxyethoxy) methyl]-[4'(2-methylpropyl)][1,1'-biphenyl]-2-sulfonamide Compound B was prepared from compound A and compound A from Example 4 as described for compound A from Example 12. Chromatography on silica gel using hexanes/ethyl acetate (3:1) afforded compound B as a colorless gum.

C. N-(3,4-Dimethyl-5-isoxazolyl)-4'-(2-methylpropyl)-[1,1'-biphenyl]-2-sulfonamide Example 21 was prepared from compound B as described for Example 18. Chromatography on silica gel using 3:1 hexanes/ethyl acetate followed by crystallization from methylene chloride/hexanes provided Example 21 as colorless prisms, m.p. 126° C.

Analysis for $C_{21}H_{24}N_2O_3S$; Calc'd: C, 65.60; H, 6.29; N, 7.29; S, 8.34. Found: C, 65.59; H, 6.16; N, 7.28; S, 8.50.

EXAMPLE 22

4-Butyl-N-(3,4-dimethyl-5-isoxazolyl)[1,1'-biphenyl]-2-sulfonamide

A. 4-Butyl-phenylboronic Acid

To a solution of 1-bromo-4-butylbenzene (6.24 g, 29.3 mmol) in tetrahydrofuran (32 mL) and ether (96 mL) at −78° C., n-butyllithium (1.6 M in hexane, 21.9 mL, 35.1 mmol) was added dropwise. The mixture was stirred at −78° C. for 30 minutes and was added over 20 minutes to a solution of trimethyl borate (6.1 g, 58.6 mmol) in ether (64 mL) at −78° C. The mixture was stirred at −78° C. for 30 minutes and at room temperature overnight. 10% aqueous hydrochloric acid (150 mL) was added, the mixture was shaken for 10 minutes, the ether layer was separated and the aqueous layer was extracted with ether (100 mL). The combined organic phases were extracted with 1 N sodium hydroxide (3×100 mL) and the combined aqueous extracts were washed once with ether, acidified to pH 1 with 6N hydrochloric acid and extracted with ether (3×100 mL). The combined organic phases were washed with water, dried (magnesium sulfate) and concentrated to give compound A (2.0 g, 38%).

B. 4'-Butyl-N-(3,4-dimethyl-5-isoxazolyl)-N-[(2-methoxyethoxy)methyl][1,1'-biphenyl]-2-sulfonamide Compound B was prepared from compound A and compound A from Example 4 as described for compound A from Example 12. Chromatography on silica gel using 40:1 methylene chloride/ethyl acetate afforded compound B as a colorless gum.

C. 4'-Butyl-N-(3,4-dimethyl-5-isoxazolyl)[1,1'-biphenyl]-2-sulfonamide

Compound C was prepared from compound B as described for Example 18, with refluxing for 8 hours. Chromatography on silica gel using 3:1 hexanes/ethyl acetate followed by crystallization from methylene chloride/hexanes provided Example 22 as colorless crystals, m.p. 92–93° C.

Analysis for $C_{21}H_{24}N_2O_3S$; Calc'd: C, 65.60; H, 6.29; N, 7.29; S, 8.34. Found: C, 65.35; H, 6.23; N, 7.29; S, 8.68.

EXAMPLE 23

N-(3,4-Dimethyl-5-isoxazolyl)-2-(1-naphthalenyl)-benzenesulfonamide

A. N-(3,4-Dimethyl-5-isoxazolyl)-N-[(2-methoxyethoxy)methyl]-2-(1-naphthalenyl)-benzenesulfonamide Compound A was prepared from 1-naphthaleneboronic acid and compound A from Example 4 as described for compound A from Example 12, with refluxing for 3.5 hours. Chromatography on silica gel using hexanes/ethyl acetate (3:1) afforded compound A as a colorless gum.

B. N-(3,4-Dimethyl-5-isoxazolyl)-2-(1-naphthalenyl)-benzenesulfonamide

Compound B was prepared from compound A as described for Example 18, using 6N hydrochloric acid and refluxing for 3 hours. Chromatography on silica gel using 3:1 hexanes/ethyl acetate followed by crystallization from methylene chloride/hexanes provided Example 23 as colorless prisms, m.p. 182–183° C.

Analysis for $C_{21}H_{18}N_2O_3S$; Calc'd: C, 66.65; H, 4.79; N, 7.40; S, 8.47. Found: C, 66.53; H, 4.79; N, 7.53; S, 8.41.

EXAMPLE 24

N-(3,4-Dimethyl-5-isoxazoly)-3'-(2-methylpropyl)-[1,1'-biphenyl]-2-sulfonamide

A. 3-Bromo-isobutylbenzene

To a solution of 1-iodo-3-bromobenzene (6.0 g, 21.2 mmol) in 100 mL of benzene at room temperature under argon, 1.2 g (1.06 mmol) of tetrakis(triphenylphosphine)palladium(0) was added and to this mixture a 2M solution in tetrahydrofuran of isobutyl magnesium bromide (10.6 mL) was added dropwise over 15 minutes. The mixture was stirred 2 hours, diluted with 100 mL of water, the organic layer was separated and the aqueous layer was extracted with 2×100 mL of ether. The combined organic extracts were dried and evaporated to provide 4.3 g of a colorless liquid, which upon distillation in vacuo provided 1.95 g (43%) of compound A as a colorless liquid; b.p. 124–125° C. (15–20 mm).

B. 3-Isobutyl-phenylboronic Acid

Compound B was prepared from compound A as described for compound A of Example 21. Crystallization from ether/hexanes provided compound B as a white solid, m.p. 84–86° C.

C. N-(3,4-Dimethyl-5-isoxazolyl)-N-[(2-methoxyethoxy)methyl]-3'-(2-Methylpropyl)[1,1'-biphenyl]-2-sulfonamide Compound C was prepared from Compound B and compound A from Example 4 as described for compound A from Example 12, with refluxing for 6 hours. Chromatography on silica gel using hexanes/ethyl acetate (3:1) afforded compound C as a colorless gum.

D. N-(3,4-Dimethyl-5-isoxazolyl)-3'-(2-methylpropyl)-[1,1'-biphenyl]-2-sulfonamide Compound D was prepared from compound C as described for Example 18, with refluxing for 10 hours. Chromatography on silica gel using 3:1 hexanes/ethyl acetate followed by reverse phase preparative high performance liquid chromatography (30×500 mm ODS S10 column using 85% solvent A (90% MeOH, 10% $H_2O$ 0.1% TFA) and 15% solvent B (10% MeOH, 90% $H_2O$, 0.1% TFA)) provided Example 24 as a colorless gum.

$^1$H NMR ($COCl_3$): d 1.04 (d, J=6.4 Hz, 6H), 1.94 (s, 3H), 2.02 (m, 1H), 2.26 (s, 3H), 2.64 (d, J=7.0 Hz, 2H), 6.66 (br s, 1H), 7.32–8.16 (m, 8H). Analysis for $C_{21}H_{24}N_2O_3S$-0.42 $H_2O$; Calc'd: C, 64.33; H, 6.39; N, 7.14; S, 8.18. Found: C, 64.31; H, 6.16; N, 7.16; S, 7.99.

EXAMPLE 25

N-(3,4-Dimethyl-5-isoxazolyl)-4'-(2-methylpropoxy)[1,1'-biphenyl]-2-sulfonamide

A. 4-(2-Methylpropoxy)-phenylboronic Acid

Compound A was prepared from 4-(2-methylpropoxy)-bromobenzene and trimethylborate as described for compound A of Example 21. Crystallization from ether/hexanes provided compound A as a white solid.

B. N-(3,4-Dimethyl-5-isoxazolyl)-N-[(2-methoxyethoxy)methyl]-4'-(2-methylpropoxy)[1,1'-biphenyl]-2-sulfonamide Compound B was prepared from compound A and compound A from Example 4 as described for compound A from Example 12, with refluxing for 4 hours. Chromatography on silica gel using 40:1 methylene chloride/ethyl acetate afforded compound C as a colorless gum.

C. N-(3,4-Dimethyl-5-isoxazolyl)-4'-(2-methylpropoxy)-[1,1'-biphenyl-2-sulfonamide Compound C was prepared from compound B as described for Example 18, with refluxing for 8 hours. Chromatography on silica gel using 15:1 methylene chloride/ethyl acetate provided Example 25 as a colorless solid, m.p. 50–53° C.

Analysis for $C_{21}H_{24}N_2O_4S$-0.7$H_2O$; Calc'd: C, 61.06; H, 6.20; N, 6.78; S, 7.76. Found: C, 61.28; H, 5.96; N, 6.66; S, 8.11.

EXAMPLE 26

N-(3,4-Dimethyl-5-isoxazolyl)-4'-(1-methylethoxy)-[1,1'-biphenyl]-2-sulfonamide

A. 4-(1-Methylethoxy)-phenylboronic Acid

Compound A was prepared from 4-(1-methylethoxy)-bromobenzene and trimethylborate as described for compound A of Example 21. Crystallization from ether/hexanes provided compound A as a white solid.

B. N-(3,4-Dimethyl-5-isoxazolyl)-N-[(2-methoxyethoxy)methyl]-4'-(1-methylethoxy)[1,1'-biphenyl]-2-sulfonamide.

Compound B was prepared from compound A and compound A from Example 4 as described for compound A from Example 12, with refluxing for 5 hours. Chromatography on silica gel using 4:1 hexanes/ethyl acetate afforded compound B as a colorless gum.

C. N-(3,4-Dimethyl-5-isoxazolyl)-4'-(1-methylethoxy)[1,1'-biphenyl]-2-sulfonamide.

Compound C was prepared from compound B as described for Example 18, with refluxing for 2 hours. Chromatography on silica gel using 4:1 hexanes/ethyl acetate provided Example 26 as a colorless solid, m.p. 49–52° C.

Analysis for $C_{20}H_{22}N_2O_4S$; Calc'd: C, 62.16; H, 5.74; N, 7.25; S, 8.30. Found: C, 61.98; H, 5.71; N, 7.12; S, 8.17.

EXAMPLE 27

N-(3,4-Dimethyl-5-isoxazolyl)-4'-(phenylmethyloxy)[1,1'-biphenyl]-2-sulfonamide

A. 4-Phenylmethyloxy-phenylboronic Acid

To a solution of 4-phenylmethyloxy-bromobenzene (6.0 g, 23 mmol) in tetrahydrofuran (25 mL) and ether (75 mL) at −78° C. under argon, butyllithium (1.6M solution in hexane, 14.25 mL) was added over 15 minutes. The mixture was stirred 15 minutes and transferred via cannula over 15 minutes to a solution of trimethylborate (4.73 g, 45.6 mmol) in 50 mL of ether at −78° C. under argon. After 30 minutes at −78° C., the solution was warmed to room temperature and stirred for a furthur 60 minutes. 10% aqueous hydrochloric acid was added (150 mL) and after 10 min the solution was extracted with ether (3×100 mL). The combined ether extracts were extracted with 1 M sodium hydroxide (3×100 mL) and the combined aqueous extracts were acidified with dilute hydrochloric acid to pH 2 and extracted with ether (3×100 mL). The combined ether extracts were washed once with water (100 mL), dried and evaporated to afford a white solid which was crystallized from ether/hexanes to provide 1.48 g (29%) of pure compound A as a white solid in two crops, m.p. 187–189° C.

B. N-(3,4-Dimethyl-5-isoxazolyl)-N-[(2-methoxyethoxy)methyl]-4'-(phenylmethyloxy)[1,1'-biphenyl]-2-sulfonamide Compound B was prepared from compound A and compound A from Example 4 as described for compound A from Example 12. Chromatography on silica gel using 3:1 hexanes/ethyl acetate afforded compound B as a colorless gum.

C. N-(3,4-Dimethyl-5-isoxazolyl)-4'-(phenylmethyloxy)-[1,1'-biphenyl]-2-sulfonamide Compound C was prepared from compound B as described for Example 18, with refluxing for 18 hours. Chromatography on silica gel using 3:1 hexanes/ethyl acetate followed by reverse phase preparative HPLC (30× 500 mm ODS S10 column using 85% solvent A (90% MeOH, 10% $H_2O$, 0.1% TFA) and 15% solvent B (10% MeOH, 90% $H_2O$, 0.1% TFA)) provided Example 27 as a colorless gum.

$^1$H NMR (CDCl$_3$): d 1.93(s, 3H), 2.20 (s, 3H), 5.20 (s, 2H), 6.32 (br s, 1H), 7.14–8.11 (m, 13H).

Analysis for $C_{24}H_{22}N_2O_4S$; Calc'd: C, 66.34; H, 5.10; N, 6.45; S, 7.38. Found: C, 66.14; H, 5.00; N, 6.29; S, 7.09.

EXAMPLE 28

4'-(1,1-Dimethylethyl)-N-(3,4-dimethyl-5-isoxazolyl)-[1,1'-biphenyl]-2-sulfonamide A. 4-t-Butyl-phenylboronic Acid Compound A was prepared from 4-t-butyl-bromobenzene and trimethylborate as described for compound A of Example 21. Crystallization from ether/hexanes provided compound A as white crystals, m.p. 201–203° C.

B. 4'-(1,1-Dimethylethyl)-N-(3,4-dimethyl-5-isoxazolyl)-N-[(2-methoxyethoxy)methyl][1,1'-biphenyl]-2-sulfonamide Compound B was prepared from compound A and compound A from Example 4 as described for compound A from Example 12, with refluxing for 4 hours. Chromatography on silica gel using 6:1 hexanes/ethyl acetate afforded compound B as a colorless gum.

C. 4'-(1,1-Dimethylethyl)-N-(3,4-dimethyl-5-isoxazolyl)-[1,1'-biphenyl]-2-sulfonamide Compound C was prepared from compound B as described for Example 18, with refluxing for 5 hours. Chromatography on silica gel using 4.5:1 hexanes/ethyl acetate followed by crystallization from ethyl acetate/hexanes provided Example 28 as colorless crystals, m.p. 169–170° C.

Analysis for $C_{21}H_{24}N_2O_3S$; Calc'd: C, 65.60; H, 6.29; N, 7.29; S, 8.34. Found: C, 65.44; H, 6.24; N, 7.26; S, 8.21.

EXAMPLE 29

N-(3,4-Dimethyl-5-isoxazolyl)-4'-methoxy-[1,1'-biphenyl]-2-sulfonamide

A. N-(3,4-Dimethyl-5-isoxazolyl)-4'-methoxy-N-[(2-methoxyethoxy)methyl][1,1'-biphenyl]-2-sulfonamide Compound A was prepared from 4-methoxybenzeneboronic acid and compound A from Example 4 as described for compound A from Example 12, using toluene rather than benzene and with heating at 95° C. for 5 hours. Chromatography on silica gel using 3.5:1 hexanes/ethyl acetate afforded compound A as a colorless gum.

B. N-(3,4-Dimethyl-5-isoxazolyl)-4'-methoxy-[1,1'-biphenyl]-2-sulfonamide

Compound B was prepared from compound A as described for Example 18, with refluxing for 4 hours. Cooling of the reaction mixture afforded Example 29 as colorless crystals, m.p. 179–181° C.

Analysis for $C_{18}H_{18}N_2O_4S$; Calc'd: C, 60.32; H, 5.06; N, 7.82; S, 8.95. Found: C, 60.14; H, 5.08; N, 7.86; S, 9.24.

EXAMPLE 30

N-(3,4-Dimethyl-5-isoxazolyl)-4'-[(1-methylethyl)amino][1,1'-biphenyl]-2-sulfonamide A. 4'-Amino-N-(3,4-dimethyl-5-isoxazolyl)-N-[(2-methoxyethoxy)methyl][1,1'-biphenyl]-2-sulfonamide Compound A was prepared from 4-amino-phenylboronic acid and compound A from Example 4 as described for compound A from Example 12, using toluene rather than benzene and with heating at 85° C. for 4 hours. Chromatography on silica gel using 1:1 hexanes/ethyl acetate afforded compound A as a colorless gum.

B. N-(3,4-Dimethyl-5-isoxazolyl)-N'-(methoxyethoxymethyl)-4'-[(1-methylethyl)amino][1,1'-biphenyl]-2-sulfonamide To compound A (720 mg, 1.67 mmol) and acetone (0.16 mL, 2.17 mmol) in 1,2-dichloroethane (12 mL) at 0° C., acetic acid (0.14 mL) was added over 5 minutes followed by sodium triacetoxyborohydride (460 mg, 2.17 mmol) in portions. The mixture was stirred at room temperature overnight, additional acetone (0.04 ml, 0.54 mmol), acetic acid (0.04 mL) and sodium triacetoxyborohydride (115 mg, 0.54 mmol) were added and the mixture was stirred 40 minutes. The mixture was poured into water (50 mL), ethyl acetate (150 mL) was added and the organic layer was separated, washed with brine, dried and concentrated. The residue was chromatographed on silica gel with 3:1 hexanes/ethyl acetate to afford compound B (590 mg, 75%) as a colorless gum.

C. N-(3,4-Dimethyl-5-isoxazolyl)-4'-[(1-methylethyl)amino][]1,1'-biphenyl]-2-sulfonamide To a solution of compound B (315 mg, 0.67 mmol) in 95% ethanol (8 mL), 6N aqueous hydrochloric acid (8 mL) was added. The mixture was refluxed for 3 hours and concentrated. Saturated sodium hydrogen carbonate was added until the pH was above 8. The mixture was acidified to ~pH 5 with acetic acid and extracted with ethyl acetate (3×30 mL). The combined organic extracts were washed with brine, dried and concentrated. The residue was chromatographed on silica gel using 2:1 hexanes/ethyl acetate to afford Example 30 as a colorless solid (225 mg, 88%), m.p. 62–64° C.

Analysis for $C_{20}H_{23}N_3O_3S$; Calc'd: C, 62.32; H, 6.01; N, 10.90; S, 8.32. Found: C, 62.32; H, 6.16; N, 10.44; S, 7.86.

EXAMPLE 31

2-[[[[2'-[[(3,4-Dimethyl-5-isoxazolyl)amino]sulfonyl][1,1'-biphenyl]-4-yl](1-methylethyl)amino]carbonyl]-amino]-4-methylpentanoic Acid, Ethyl Ester A. 2-[[[[2'-[[(3,4-Dimethyl-5-isoxazolyl)amino]carbonyl]-[1,1'-biphenyl]-4-yl](1-methylethyl)amino]carbonyl]-amino]-4-methylpentanoic Acid, Ethyl Ester To a solution of Example 30 (145 mg, 0.38 mmol) in methylene chloride (4.4 mL), ethyl 2-isocyanato-4-methyl valerate (163 mg, 0.88 mmol) was added. The mixture was stirred for two days, diluted with ethyl acetate (25 mL) and washed with water (20 mL) and brine. The organic phase was dried and concentrated and the residue was chromatographed on silica gel using 3:2 hexanes/ethyl acetate to afford Example 31 as a colorless solid (190 mg, 85%), m.p. 58–61° C.

Analysis for $C_{29}H_{38}N_4O_6S$; Calc'd: C, 61.03; H, 6.71; N, 9.82; S, 5.62. Found: C, 60.59; H, 6.97; N, 9.46; S, 5.29.

EXAMPLE 32

2'-Amino-N-(3,4-dimethyl-5-isoxazolyl)-4'-(2-methyl-propyl)[1,1'-biphenyl]-2-sulfonamide A. 4-Isobutyl-2-nitro-phenylboronic Acid To a suspension of 4-isobutyl-phenylboronic acid (0.9 g, 5.05 mmol) in acetic anhydride (9 mL) at −10° C., fuming nitric acid (0.4 mL) was added over 10 minutes. The mixture was stirred for 1 hour, warmed to room temperature and stirred for an additional 1.5 hours. The clear orange solution was added to 100 mL of ice, stirred for 3 hours and azeotroped with water (4×100 mL). The residue was partitioned between 25 mL each of ether and water and the ether layer was dried and evaporated to provide 0.75 g of yellow solid. The solid was dissolved in ethyl acetate (25 mL) and the solution was extracted with 1 N aqueous sodium hydroxide (2×25 mL). The combined aqueous extracts were acidified to pH 2 using 2N aqueous hydrochloric acid and extracted with ethyl acetate (2×25 mL). The combined organic extracts were washed once with water, dried and evaporated to provide 0.63 g of light yellow solid. Reverse phase preparative HPLC on a 30×500 mm ODS S10 column using 76% solvent A (90% MeOH, 10% $H_2O$, 0.1% TFA) and 24% solvent B (10% MeOH, 90% $H_2O$, 0.1% TFA) provided 0.16 g of compound A as light yellow solid.

B. 4-Isobutyl-2-amino-phenylboronic Acid

To a suspension of 0.1 g of 10% Pd/C in 10 mL of methanol under argon, 0.32 g (1.4 mmol) of compound A in 10 mL of methanol was added and the mixture was hydrogenated at 60 psi for 6 hours. The mixture was filtered and the filtrate concentrated to provide 0.3 g of compound B as a brown residue.

C. 2'-Amino-N-(3,4-dimethyl-5-isoxazolyl)-N-[(2-methoxyethoxy)methyl]-4'-(2-methylpropyl)[1,1'-biphenyl]-2-sulfonamide Compound C was prepared from compound B and compound A from Example 4 as described for compound A from Example 12, with refluxing for 6 hours. Chromatography on silica gel using 3:1 hexanes/ethyl acetate afforded compound C as a colorless gum.

D. 2'-Amino-N-(3,4-dimethyl-5-isoxazolyl)-4'-(2-methylpropyl)[1,1'-biphenyl]-2-sulfonamide Compound D was prepared from compound C as described for Example 12, with refluxing for 3 hours. Preparative reverse phase high performance liquid chromatography (30×500 mm ODS S10 column using 60% solvent A (90% MeOH, 10% $H_2O$, 0.1% TFA) and 40% solvent B (10% MeOH, 90% $H_2O$, 0.1% TFA)) followed by chromatography on silica gel using 2% methanol in methylene chloride afforded 0.05 g of Example 32, as a light brown foam. m.p. 60–70° C. (amorphous).

Analysis for $C_{21}H_{25}N_3O_3S \cdot 0.44\ H_2O$; Calc'd: C, 61.90; H, 6.40; N, 10.31; S, 7.87. Found: C, 61.98; H, 6.23; N, 10.23; S, 7.73.

EXAMPLE 33

N-[2'-[[(3,4-Dimethyl-5-isoxazolyl)amino]sulfonyl][1,1'-biphenyl]-4-yl]]-N-(1-methylethyl)-β-phenylbenzenepropanamide A. N-(3,4-Dimethyl-5-isoxazolyl)-N'-(methoxyethoxymethyl)-4'-[(1-methylethyl)-(3,3-diphenyl-1-oxopropyl)-amino]-[1,1'-biphenyl]-2-sulfonamide To compound B from Example 30 (60 mg, 0.13 mmol) in methylene chloride (1.3 mL), 3,3-diphenylpropionyl chloride (93 mg, 0.38 mmol) and triethylamine (0.07 mL) were added. The mixture was stirred 2.5 hours, diluted with ethyl acetate (20 mL) and washed with saturated ammonium chloride (2×15 mL) and brine, dried and concentrated. The residue was chromatographed on silica gel using 1:1 hexanes/ethyl acetate to afford compound A as a colorless gum (45 mg, 52%).

B. N-[2'-[[(3,4-Dimethyl-5-isoxazolyl)amino]sulfonyl][1,1'-biphenyl]-4-yl]]-N-(1-methylethyl)-β-phenylbenzenepropanamide Example 33 was prepared from compound A as described for Example 18, with refluxing for 3 hours. Chromatography on silica gel using 3:1 methylene chloride/ethyl acetate provided Example 33 as a light yellow solid, m.p. 177° C.

Analysis for $C_{35}H_{35}N_3O_4S \cdot 0.4 H_2O$; Calc'd: C, 69.96; H, 6.00; N, 6.99; S, 5.34. Found: C, 70.13; H, 6.10; N, 6.82; S, 5.21.

EXAMPLE 34

2'-Nitro-N-(3,4-dimethyl-5-isoxazolyl)-[1,1'-biphenyl]-2-sulfonamide

A. 2'-Nitro-N-(3,4-dimethyl-5-isoxazolyl)-N-(methoxyethoxymethyl)[1,1'-biphenyl]-2-sulfonamide Compound A was prepared from 2-nitrophenylboronic acid and compound A from Example 4 as described for compound A from Example 12, using toluene in place of benzene and refluxing for 6 hours. Flash chromatography on silica gel using hexanes/ethyl acetate (2:1) provided compound A as a light yellow gum.

B. 2'-Nitro-N-(3,4-dimethyl-5-isoxazolyl)-[1,1'-biphenyl]-2-sulfonamide

Example 34 was prepared from compound A as described for Example 12, with refluxing for 4 hours. Flash chromatography on silica gel using hexanes/ethyl acetate (2:1) followed by crystallization from hexanes/ethyl acetate afforded Example 34 as light brown needles, m.p. 128–130° C.

Analysis calculated for $C_{17}H_{15}N_3O_5S$; Calc'd: C, 54.69; H, 4.05; N, 11.25; S, 8.59. Found: C, 54.67; H, 3.88; N, 11.17; S, 8.59.

EXAMPLE 35

5-[[(2-Phenyl)phenyl]sulfonyl]amino]-3-methyl-4-isoxazolecarboxylic Acid, Ethyl Ester A. [1,1'-Biphenyl]-2-sulfonamide To a degassed solution of 2-bromobenzenesulfonamide (0.7 g, 3.0 mmol) and tetrakis(triphenylphosphine) palladium (0) (0.21 g, 0.18 mmol) in benzene (25 mL) was added 2M aqueous sodium carbonate (15 mL) followed by a solution of phenylboronic acid (0.44 g, 3.6 mmol) in 95% ethanol (25 mL). The yellow two phase solution was refluxed for 18 hours, cooled to room temperature and diluted with water (100 mL). The solution was extracted with ethyl acetate (2×100 mL) and the combined organic phases were washed with brine, dried (magnesium sulfate), filtered and evaporated. The residue was chromatographed on silica gel with hexanes/ethyl acetate (2:1) to yield 250 mg (36%) of compound A as a yellow solid.

B. 5-[[(2-Phenyl)phenyl]sulfonyl]amino]-3-methyl-4-isoxazolecarboxylic Acid, Ethyl Ester A solution of compound A (187 mg, 0.82 mmol), 3-methyl-4-ethoxycarbonyl-5-bromoisoxazole (197 mg, 0.42 mmol) and cesium carbonate (274 mg, 0.42 mmol) in dry dimethylformamide (4 mL) was heated at 55° C. for 18 hours. The solution was cooled to room temperature, diluted with water (40 mL) and acidified to pH 4 with 6N aqueous hydrogen chloride. The tan precipitate was collected by filtration, rinsed with water, and dried to afford 110 mg (36%) of Example 35 as a tan solid, m.p. 126–128° C.

Analysis calculated for $C_{19}H_{18}N_2O_5S$-0.35 $H_2O$; Calc'd: C, 58.10; H, 4.80; N, 7.13; S, 8.16. Found: C, 58.19; H, 4.59; N, 7.04; S, 8.06.

EXAMPLE 36

N-(3-Methyl-4-phenylmethyl-5-isoxazolyl)-4'-(2-methylpropyl)-[1,1'-biphenyl]-2-sulfonamide A. N-(2-Bromobenzenesulfonyl)-pyrrole Potassium hydride (35% oil dispersion, 5.76 g, 50 mmol; washed three times with hexanes) was covered with dry tetrahydrofuran (200 mL) and the suspension was cooled to 0° C. Pyrrole (passed through activity I basic alumina, 4.16 ml, 60 mmol) in tetrahydrofuran (60 mL) was added dropwise over 20 min. The ice bath was removed and the solution was allowed to stir at ambient temperature until the gas evolution ceased (20 minutes) whereupon 2-bromobenzenesulfonyl chloride (10.22 g, 40 mmol) in tetrahydrofuran (60 mL) was added dropwise over 20 minutes. After stirring for 1 hour, the mixture was filtered through Celite AFA and the filter pad was rinsed with tetrahydrofuran (100 mL). The filtrate was evaporated and the resulting white solid was recrystallized from methanol to afford 7.47 g (65%) of compound A, mp 85.0–87.0° C.

B. N-(4'-(2-Methylpropyl)-1,1'-biphenylsulfonyl)-pyrrole

Compound B was prepared from compound A and compound A from Example 21 as described for compound A from example 12, using toluene rather than benzene and with heating at 80° C. for 2 hours. Chromatography on silica gel using 1:1 hexanes/methylene chloride afforded compound B as an oil.

C. 4'-(2-Methylpropyl)-1,1'-biphenyl-2-sulfonic Acid, Sodium Salt

A solution of compound B and 5N sodium hydroxide (53 mL) in methanol (70 mL) was refluxed for 6.5 hours. Evaporation of the methanol afforded a white solid which was collected and dried under vacuum. Recrystallization from water (40 mL) afforded 3.05 g (88%) of compound C as a white solid.

D. 4'-(2-Methylpropyl)-1,1'-biphenyl-2-sulfonylchloride

Compound C (1.6 g, 5 mmol) and phosphorus pentachloride (3.1 g, 15 mmol) were ground together with a glass rod and the mixture was heated at 60° C. for 2.5 hours. Ice water was added and the mixture was extracted twice with ethyl acetate. The combined organic layers were washed with brine, dried (magnesium sulfate) and evaporated to afford 1.45 g (94%) of compound D.

E. N-(3-Methyl-4-phenylmethyl-5-isoxazolyl)-4'-(2-methylpropyl)-[1,1'-biphenyl]-2-sulfonamide Compound D (0.15 g, 0.48 mmol) in pyridine (0.1 mL) was added to a solution of 3-methyl-4-phenylmethyl-5-isoxazolamine (0.12 g, 0.64 mmol) and dimethylaminopyridine (13 mg, 0.1 mmol) in pyridine (0.2 mL). The solution was stirred at 75° C. for 2.5 hours, cooled to room temperature and diluted with water. The solution was adjusted to pH 3 with 1N hydrochloric acid and extracted with ether (2×50 ml). The combined organic layers were washed with brine, dried (magnesium sulfate) and evaporated. The residue was subjected to flash chromatography (silica, 7% ethyl acetate/methylene chloride) and the partially purified material was subjected to flash chromatography (silica, ether) to afford 30 mg (15%) of pure Example 36 as an oil which solidified upon standing, mp 137.0–138.5° C.;

Analysis calculated for $C_{27}H_{28}N_2O_3S$-0.86 $H_2O$; Calc'd: C, 68.12; H, 6.29; N, 5.88; S, 6.73. Found: C, 68.38; H, 6.04; N, 6.23; S, 6.31.

EXAMPLE 37

N-(4,5-Dimethyl-3-isoxazolyl)-4'-(2-methylpropyl)-[1,1'-biphenyl]-2-sulfonamide

Compound D of Example 36 (0.56 g, 1.8 mmol) in pyridine (0.8 mL) was added to a solution of 4,5-dimethyl-3-isoxazolamine (0.25 g, 2.2 mmol) and 4-dimethylaminopyridine (44 mg, 0.4 mmol) in pyridine (0.7 mL). The solution was stirred at 75° C. for 2.5 hours, cooled to room temperature and diluted with water (10 mL). The solution was adjusted to pH 3 with 6N hydrochloric acid and extracted with ether (2×80 mL). The combined organic layers were washed with brine, dried (magnesium sulfate) and evaporated. Flash chromatography (silica, 20% ethyl acetate/hexanes) afforded 0.33 g (48%) of Example 37.

Recrystallization from ether/hexane afforded an analytical sample as a white crystalline solid, mp 131.5–133.0° C.

Analysis calculated for $C_{21}H_{24}N_2O_3S$; Calc'd: C, 65.60; H, 6.29; N, 7.29; S, 8.34. Found: C, 65.64; H, 6.33; N, 7.32; S, 8.31.

EXAMPLE 38

4'-(2-Methylpropyl)-2'-Methoxy-N-(3,4-dimethyl-5-isoxazolyl)-[1,1'-biphenyl]-2-sulfonamide A. 4-Isobutyl-2-methoxy-phenylboronic Acid To a solution of 4-(2-methylpropyl)-2-methoxybenzene (4.0 g, 24 mmol) in ether (100 mL) under argon at –78° C., tetramethylethylenediamine (11 mL, 73 mmol) was added followed by t-butyllithium (1.7 M solution in pentane, 43 mL) added over 5 minutes. The mixture was warmed to room temperature, stirred for 5 hours, cooled to –78° C. and trimethylborate (7.6 g) was added in one portion. The solution was warmed to room temperature, stirred overnight, cooled to 0° C. and 20% aqueous hydrochloric acid (250 mL) was added. The solution was extracted with ether and the combined ether extracts were extracted three times with 1 M sodium hydroxide. The precipitate which formed was collected and added to the combined aqueous extracts. This mixture was acidified with dilute hydrochloric acid to pH 2 and the solution was extracted twice with ether. The combined ether extracts were washed once with water, dried and evaporated. The white solid was crystallized from hexanes in two crops to provide 2.1 g (42%) of compound A as a white solid, m.p. 68–75° C.

B. 4'-(2-Methylpropyl)-2'-Methoxy-N-(3,4-dimethyl-5-isoxazolyl)-N-(methoxyethoxymethyl)[1,1'-biphenyl]-2-sulfonamide Compound B was prepared from compound A and compound A from Example 4 as described for compound A from Example 12, using toluene in place of benzene and refluxing for 6 hours. Flash chromatography on silica gel using hexanes/ethyl acetate (3:1) provided compound B as a colorless gum.

C. 4'-(2-Methylpropyl)-2'-Methoxy-N-(3,4-dimethyl-5-isoxazolyl)-[1,1'-biphenyl]-2-sulfonamide Example 38 was prepared from compound B as described for Example 12, using 6N hydrochloric acid and with refluxing for 3 hours. Crystallization from hexanes/ethyl acetate afforded Example 38 as a white crystalline solid, m.p. 143–144° C.

Analysis calculated for $C_{22}H_{26}N_2O_4S \cdot 0.38H_2O$; Calc'd: C, 62.71; H, 6.40; N, 6.65; S, 7.61. Found: C, 62.77; H, 6.35; N, 6.59; S, 7.85.

EXAMPLE 39

4'-(2-Methylpropyl)-2'-hydroxy-N-(3,4-dimethyl-5-isoxazolyl)-[1,1'-biphenyl]-2-sulfonamide To a solution of Example 38 (0.3 g, 0.72 mmol) in dry methylene chloride (25 mL) at –78° C. under argon, boron tribromide (1.1 mL of a 1M solution in methylene chloride) was added. The solution was stirred for 3 hours at –78° C. and was stirred overnight as it warmed to room temperature. The solution was diluted with methylene chloride, washed twice with water, dried and evaporated. The residue was chromatographed on silica gel using 1% methanol/methylene chloride and the white foamy solid was crystallized from hexanes/ethyl acetate to afford 0.1 g of Example 39 as colorless prisms, m.p. 175° C.

Analysis calculated for $C_{21}H_{24}N_2O_4S \cdot 0.46H_2O$; Calc'd: C, 61.70; H, 6.14; N, 6.85; S, 7.84. Found: C, 61.70; H, 6.12; N, 6.66; S, 7.99.

EXAMPLE 40

N-(3-Methyl-4-nitro-5-isoxazolyl)-4'-(2-methylpropyl)-[1,1'-biphenyl]-2-sulfonamide Example 40 was prepared from compound D of Example 36 and 3-methyl-4-nitro-5-isoxazolamine as described for Example 37, with stirring at room temperature for 5 days. After flash chromatography (silica, 50% ethyl acetate/methylene chloride), the crude product was partitioned between ethyl acetate and water taken to pH 1 with 6 N hydrochloric acid. The aqueous phase was extracted twice with ethyl acetate and the combined organic phases were washed with brine, dried (magnesium sulfate) and evaporated. Recrystallization from methylene chloride/hexanes afforded Example 40 as a yellow crystalline solid, mp 124–126° C.

Analysis calculated for $C_{20}H_{21}N_3O_5S$; Calc'd: C, 57.82; H, 5.09; N, 10.11; S, 7.72. Found: C, 57.89; H, 5.12; N, 10.25; S, 7.72.

EXAMPLE 41

N-(4-Methyl-5-isoxazolyl)-4'-(2-methylpropyl)-[1,1'-biphenyl]-2-sulfonamide

Example 41 was prepared from compound D of Example 36 and 4-methyl-5-isoxazolamine as described for Example 37, with stirring at room temperature for 2.2 hours. Flash chromatography (silica, 10% ethyl acetate/methylene chloride) followed by trituration with ether afforded Example 41 as a white crystalline solid, mp 153.0–155.5° C.

Analysis calculated for $C_{20}H_{22}N_2O_3S \cdot 0.39\ H_2O$; Calc'd: C, 63.65; H, 6.08; N, 7.42; S, 8.49. Found: C, 63.39; H, 5.90; N, 7.68; S, 8.40.

EXAMPLE 42

4'-(2-Methylpropyl)-N-(4,5,6,7-tetrahydro-2,1-benzisoxazol-3-yl)-[1,1'-biphenyl]-2-sulfonamide Example 42 was prepared from compound D of Example 36 and 4,5,6,7-tetrahydro-2,1-benzisoxazol-3-amine as described for Example 37, with stirring at 75° C. for 2 hours. Flash chromatography (silica, 30% ethyl acetate/methylene chloride) followed by a second flash chromatography (silica, ether) followed by recrystallization from methylene chloride/hexanes afforded Example 42 as an off-white crystalline solid, mp 111.0–114.5° C.

Analysis calculated for $C_{23}H_{26}N_2O_3S$; Calc'd: C, 67.29; H, 6.38; N, 6.82; S, 7.81. Found: C, 66.93; H, 6.36; N, 7.04; S, 7.57.

EXAMPLE 43

5-Amino-4'-(2-methylpropyl)-N-(3,4-dimethyl-5-isoxazolyl)-[1,1'-biphenyl]-2-sulfonamide A. 2-Bromo-4-(1-oxoethylamino)-benzenesulfonyl Chloride To 2-bromo-4-(1-oxoethylamino)-benzene (6.2 g, 29 mmol) was added chlorosulfonic acid (20 mL). The solution was heated at 57° C. for 3 hours, an additional 10 mL of chlorosulfonic acid was added and the solution was heated at 67° C. for 6 hours. The mixture was added dropwise to ice water and the heterogeneous mixture was extracted with ethyl acetate. The organic extract was washed once with brine, dried (magnesium sulfate) and evaporated. The residue was dissolved in ethyl acetate (50 mL) and the solution was filtered. The insoluble solid was rinsed twice with ethyl acetate and the combined filtrates were evaporated to afford 6.9 g (82%) of crude compound A as a brown foamy gum.

B. 2-Bromo-4-(1-oxoethylamino)-N-(3,4-dimethyl-5-isoxazolyl)-benzenesulfonamide

A solution of crude compound A (6.9 g, 22 mmol), 3,4-dimethyl-5-isoxazolamine (3.96 g, 35.3 mmol) and dimethylaminopyridine (0.42 g, 3.5 mmol) in pyridine (25 mL) was heated at 78° C. for 3.5 hours. The solvent was evaporated and the residue was partitioned between ethyl acetate and aqueous potassium hydrogen sulfate. The aqueous layer was washed with ethyl acetate and the combined organic layers were washed with brine, dried (magnesium sulfate) and evaporated. The brown solid was subjected to flash chromatography on silica with 90% ethyl acetate/hexanes to afford 3.72 g (43%) of crude compound B as a yellow foam.

C. 2-Bromo-4-(1-oxoethylamino)-N-(methoxyethoxymethyl)-N-(3,4-dimethyl-5-isoxazolyl)-benzenesulfonamide To sodium hydride (0.32 g of an 80% oil dispersion, washed three times with hexanes; 10.5 mmol) was added dropwise compound A (3.72 g, 9.6 mmol) in dry tetrahydrofuran (75 mL). The resulting suspension was cooled to 0° C. and methoxyethoxymethylchloride (1.09 mL, 9.6 mmol) in dry tetrahydrofuran (10 mL) was added dropwise. The solution was allowed to warm to room temperature overnight, ethyl acetate was added and the solution was extracted with aqueous sodium hydrogen carbonate and brine, dried (magnesium sulfate) and evaporated to afford 3.82 g of a yellow foamy gum. Flash chromatography on silica with 80% ethyl acetate/hexanes afforded 0.52 g (11%) of clean compound C as a yellow foamy gum as well as 0.92 g of less pure material.

D. 4'-(2-Methylpropyl)-4-(1-oxoethylamino)-N-(methoxyethoxymethyl)-N-(3,4-dimethyl-5-isoxazolyl)-[1, 1'-biphenyl]-2-sulfonamide Compound D was prepared from compound C and 4-(2-methylpropyl)-benzeneboronic acid as described for compound A of Example 12, using toluene rather than benzene, with heating at 84° C. for 90 minutes. Flash chromatography on silica gel using hexanes/ethyl acetate (1:1) afforded compound D as a colorless gum.

E. 5-Amino-4'-(2-methylpropyl)-N-(3,4-dimethyl-5-isoxazolyl)-[1,1'-biphenyl]-2-sulfonamide A solution of compound D (0.40 g, 0.75 mmol) in a 1:1 mixture of 6N hydrochloric acid:95% ethanol (30 mL) was heated at reflux for 4.5 hours. The ethanol was evaporated and the aqueous solution was taken to pH 3.5 with aqueous sodium hydrogen carbonate and extracted three times with ethyl acetate. The combined organic phases were washed with brine, dried (magnesium sulfate) and evaporated. Flash chromatography on silica with 25%, then 33% ethyl acetate/hexanes afforded 40 mg of Example 43 as a white foamy solid, m.p. 69–79° C.

Analysis calculated for $C_{21}H_{25}N_3O_3S \cdot 0.18H_2O$; Calc'd: C, 62.63; H, 6.35; N, 10.43; S, 7.96. Found: C, 63.03; H, 6.62; N, 10.03; S, 7.55.

EXAMPLE 44

2'-Fluoro-4'-(2-methylpropyl)-N-(3,4-dimethyl-5-isoxazolyl)-[1,1'-biphenyl]-2-sulfonamide A. 3-Fluoro-(2-methyl-1-propenyl)-benzene To a solution of isopropyl triphenylphosphonium iodide (32 g, 74 mmol) in ether (620 mL) at −15° C., n-butyllithium (1.6 M in hexane, 55 mL, 88 mmol) was added dropwise. The mixture was stirred at room temperature for 3 hours, cooled to −78° C., and 3-fluorobenzaldehyde (10.1 g, 81 mmol) was added slowly. The mixture was stirred at room temperature overnight, cold water was added and the mixture was stirred for several minutes and filtered. The organic phase of the filtrate was separated and washed three times with water, dried (magnesium sulfate), filtered and concentrated. The residue was chromatographed on silica gel with pentane to afford 10 g of compound A (90%) as a colorless liquid.

B. 3-Fluoro-(2-methylpropyl)-benzene

A mixture of compound A (8 g, 53 mmol) and 10% palladium on carbon (1.2 g) in ethyl acetate (80 mL) was hydrogenated at 60 psi for 1 hour. The mixture was filtered, the filtrate was concentrated and the residue was distilled under vacuum to afford compound B as a colorless liquid (5.9 g, 74%), b.p. 113° C./150 mmHg.

C. 2-Fluoro-4-(2-methylpropyl)-phenylboronic Acid

Compound C was prepared from compound B as described for compound A of Example 38, with the following changes. The t-butyllithium solution was stirred at −78° C. for 5 hours. Initial extractions were performed with methylene chloride and the combined organic phases were concentrated to 100 mL before base extraction, during which no precipitate was observed. Trituration with hexanes afforded compound C as a white solid, m.p. 96–100° C.

D. 2'-Fluoro-4'-(2-methylpropyl)-N-(methoxyethoxymethyl)-N-(3,4-dimethyl-5-isoxazolyl)-[1, 1'-biphenyl]-2-sulfonamide Compound D was prepared from compound C and compound A from Example 4 as described for compound A of Example 12, using toluene rather than benzene, with heating at 80° C. for 3 hours. Flash chromatography on silica gel using hexanes/ethyl acetate (4:1) afforded compound D as a colorless gum.

E. 2'-Fluoro-4'-(2-methylpropyl)-N-(3,4-dimethyl-5-isoxazolyl)-[1,1'-biphenyl]-2-sulfonamide Example 44 was prepared from compound D as described for Example 12, using 6N hydrochloric acid and with refluxing for 3 hours. Flash chromatography on silica gel using hexanes/ethyl acetate (3:1) followed by crystallization from hexanes/ethyl acetate afforded Example 44 as colorless crystals, m.p. 139–141° C.

Analysis calculated for $C_{21}H_{23}N_2O_3FS$. Calc'd: C, 62.67; H, 5.76; F, 4.72; N, 6.96; S, 7.97. Found: C, 62.81; H, 5.83; F, 4.59; N, 6.97; S, 8.03.

EXAMPLE 45

5-Methoxy-4'-(2-methylpropyl)-N-(3,4-dimethyl-5-isoxazolyl)-[1,1'-biphenyl]-2-sulfonamide A. N-(3,4-Dimethyl-5-isoxazolyl)-2-bromo-4-methoxy-benzenesulfonamide To chlorosulfonic acid (10 mL) at 0° C. was added dropwise 3-bromoanisole (9.3 g, 50 mmol) at such a rate that the internal temperature remained below 5° C. The mixture was stirred at 0° C. for 2 hours and added dropwise to crushed ice. The mixture was extracted three times with methylene chloride and the combined organic layers were dried (sodium sulfate) and concentrated to afford a mixture of 2-bromo-4-methoxy-benzenesulfonyl chloride and 4-bromo-2-methoxy-benzenesulfonyl chloride (756 mg, 5%) as a colorless oil. A solution of this material (756 mg, 1 mmol), 3,4-dimethyl-5-isoxazolamine (386 mg, 3.44 mmol) and 4-dimethylaminopyridine (65 mg, 0.53 mmol) in dry pyridine (5 mL) was heated at 70° C. for 2 hours. The mixture was cooled to room temperature and was poured into water. The pH of the mixture was adjusted to 8 with saturated sodium bicarbonate solution and the mixture was extracted twice with ether. The aqueous layer was brought to pH 2 with 6 N hydrochloric acid and was extracted three times with ether. These organic extracts were combined, dried (sodium sulfate) and concentrated to provide a mixture of compound A and the regiomeric N-(3,4-dimethyl-5-isoxazolyl)-4-bromo-2-methoxy-benzenesulfonamide as a tan foam (743 mg). Chromatography (flash, silica, 2% methanol/chloroform) provided pure compound A (288 mg, 30%).

B. 2-Bromo-4-methoxy-N-(methoxyethoxymethyl)-N-(3,4-dimethyl-5-isoxazolyl)-benzenesulfonamide To a 0° C. suspension of sodium hydride (60% oil dispersion, 33.5 mg, 0.837 mmol) in dry tetrahydrofuran (2 mL) was added dropwise a solution of compound A (288 mg, 0.797 mmol) in dry tetrahydrofuran (4 mL). After stirring at 0° C. for 30 min, methoxyethoxymethyl chloride (0.100 mL, 0.877 mmol) was added dropwise. After 2 hours, an additional portion of methoxyethoxymethyl chloride (0.015 mL) was added. After an additional 1 hour, the mixture was poured into saturated sodium chloride and 1 N hydrochloric acid was added. The mixture was extracted three times with ethyl acetate and the combined organic layers were dried (magnesium sulfate) and concentrated. Chromatography (flash, silica, 30% ethyl acetate/hexanes) provided compound B as a transparent oil (293 mg, 88%).

C. 4-Methoxy-4'-(2-methylpropyl)-N-(methoxyethoxymethyl)-N-(3,4-dimethyl-5-isoxazolyl)-[1,1'-biphenyl]-2-sulfonamide Compound C was prepared from compound B and 4-(2-methylpropyl)-benzeneboronic acid as described for compound A of Example 12, using toluene rather than benzene, with heating at reflux for 30 minutes. Flash chromatography on silica gel using hexanes/ethyl acetate (4:1) afforded compound D as a colorless gum. Chromatography (flash, silica, 30% ethyl acetate/hexanes) yielded compound C as a colorless oil (292 mg, 81%).

D. 4-Methoxy-4'-(2-methylpropyl)-N-(3,4-dimethyl-5-isoxazolyl)-[1,1'-biphenyl]-2-sulfonamide Example 45 was prepared from compound C as described for Example 12, using 6N hydrochloric acid and with heating at 80° C. for 19 hours. Flash chromatography on silica gel using hexanes/ethyl acetate (2:1) afforded Example 45 as a colorless glassy solid.

Analysis calculated for $C_{22}H_{26}N_2O_4S \cdot 0.11H_2O$. Calc'd: C, 63.44; H, 6.35; N, 6.76; S, 7.97. Found: C, 63.52; H, 6.34; N, 6.65; S, 8.03.

EXAMPLE 46

2'-Amino-N-(3,4-dimethyl-5-isoxazolyl)-4'-(2-methyl-propyl)[1,1'-biphenyl]-2-sulfonamide A. 3-(2-Methyl-1-propenyl)-nitrobenzene To isopropyl triphenylphosphonium iodide (74 g, 170 mmol) in 1:1 ether:tetrahydrofuran (850 mL) at −15° C., n-butyllithium (1.6 M in hexane, 118 mL, 188 mmol) was added dropwise. The mixture was stirred at room temperature for 3 hours, cooled to −50° C., and a solution of 3-nitrobenzaldehyde (28.4 g, 188 mmol) in tetrahydrofuran (60 mL) was added slowly. The mixture was stirred at room temperature overnight, cold water and hexane were added and the mixture was stirred for several minutes and filtered. The organic phase of the filtrate was separated and washed three times with water, dried (magnesium sulfate) and concentrated. The residue was chromatographed on silica gel with 50:1 hexanes/ethyl acetate to afford compound A (23 g, 76%) as a light yellow liquid.

B. 3-(2-Methyl-1-propenyl)-aniline

A mixture of compound A (4.0 g, 22 mmol) and 5% Pt/C (400 mg) in methanol (40 mL) was hydrogenated at 45 psi overnight. The mixture was filtered and the filtrate concentrated to provide compound B (3.11 g, 92%).

C. N-(2,2-Dimethyl-1-oxopropyl)-3-(2-methyl-1-propenyl)-aniline

To compound B (3.11 g, 21.1 mmol) and trimethylacetyl chloride (3.31 g, 27.5 mmol) in methylene chloride (53 mL) at 0° C., triethylamine (4.28 g, 42.2 mmol) was added slowly. The mixture was stirred at 0° C. for 1 hour and at room temperature for 15 minutes and poured into ice water. The aqueous layer was extracted twice with ethyl acetate and the combined organic phases were washed with brine, dried and concentrated. The residue was chromatographed on silica gel with 25:2 hexanes/ethyl acetate to provide compound C (3.81 g, 78%) as a white solid.

D. N-(2,2-Dimethyl-1-oxopropyl)-3-(2-methyl-1-propyl)-aniline

A mixture of compound C (3.47 g, 15 mmol) and 10% Pd/C (520 mg) in ethyl acetate (35 mL) was hydrogenated at 60 psi for 1 hour. The mixture was filtered and the filtrate concentrated to provide compound D (3.41 g, 98%).

E. 2-(2,2-Dimethyl-1-oxo-1-propylamino)-4-(2-methyl-1-propyl)-phenylboronic Acid To compound D (2.86 g, 12.3 mmol) and tetramethylethylenediamine (4.28 g, 36.8 mmol) in ether (25 mL) at −40° C., t-butyllithium (1.7 M in pentane, 21.6 mL, 36.8 mmol) was added dropwise. The solution was stirred at room temperature for 2.5 hours, cooled to −20° C. and trimethylborate (3.82 g, 36.8 mmol) was added slowly. The mixture was stirred at −10° C. to 0° C. for 1 hour and at room temperature for 3 hours, cooled to 0° C. and 10% aqueous hydrochloric acid was added. The aqueous layer was extracted three times with methylene chloride and the combined organic phases were washed with brine, dried and concentrated. The residue was triturated with ether to afford compound E as a white solid (2.52 g, 74%), m.p.>250° C.

F. 2'-(2,2-Dimethyl-1-oxo-1-propylamino)-N-(3,4-dimethyl-5-isoxazolyl)-N-[(2-methoxyethoxy)methyl]-4'-(2-methyl-propyl)[1,1'-biphenyl]-2-sulfonamide Compound F was prepared from compound E and compound A from Example 4 as described for compound A from Example 12, using toluene in place of benzene and heating at 75° C. for 7 hours. Flash chromatography on silica gel using hexanes/ethyl acetate (4:1) provided compound F as a colorless gum.

G. 2'-Amino-N-(3,4-dimethyl-5-isoxazolyl)-4'-(2-methyl-propyl)[1,1'-biphenyl]-2-sulfonamide To a solution of compound F (354 mg, 0.62 mmol) in 95% ethanol (20 mL), 50% sulfuric acid (20 mL) was added and the mixture was heated at reflux for 3.5 hours. The mixture was cooled and poured onto iced 30% ammonium hydroxide. The mixture was acidified to pH<5 with acetic acid and extracted four times with ethyl acetate. The combined organic extracts were washed with brine, dried and concentrated. Preparative HPLC (30×500 mm ODS S10 column using 65% solvent A (90% methanol, 10% water, 0.1% trifluoroacetic acid) and 35% solvent B (10% methanol, 90% water, 0.1% trifluoroacetic acid)) provided a solid which was further purified by chromatography on silica using 2% methanol/methylene chloride to afford Example 46 as a white solid, m.p. 60–70° C. (amorphous).

Analysis calculated for $C_{21}H_{25}N_3O_3S \cdot 0.25H_2O$. Calc'd: C, 62.44; H, 6.36; N, 10.40; S, 7.94. Found: C, 62.65; H, 6.23; N, 10.19; S, 7.67.

EXAMPLE 47

N-(3,4-Dimethyl-5-isoxazolyl)-4'-(3-methylbutyl)-[1,1'-biphenyl]-2-sulfonamide

A. 4-(3-Methylbutyl)-benzeneboronic Acid

Compound A was prepared from 4-(3-methylbutyl)-bromobenzene as described for Compound A from Example 21. Crystallization from hexane provided compound A as a white crystalline solid, m.p. 142° C.

B. N-(3,4-Dimethyl-5-isoxazolyl)-N-[(2-methoxyethoxy)]methyl]-[4'-(3-methylbutyl)][1,1'-biphenyl]-2-sulfonamide Compound B was prepared from compound A and compound A from Example 4 as described for compound A from Example 12, using toluene in place of benzene and with heating at 80° C. for 3 hours. Chromatography on silica gel using 6:1 hexanes/ethyl acetate afforded compound B as a colorless gum.

C. N-(3,4-Dimethyl-5-isoxazolyl)-4'-(3-methylbutyl)-[1,1'-biphenyl]-2-sulfonamide The title compound was prepared from compound B as described for Example 18, with refluxing for 4.5 hours. The mixture was cooled and filtered to provide the title compound as a white crystalline solid, m.p. 125–127° C.

Analysis for $C_{22}H_{26}N_2O_3S$. Calc'd: C, 66.31; H, 6.58; N, 7.03; S, 8.04. Found: C, 66.43; H, 6.58; N, 7.10; S, 8.02.

EXAMPLE 48

N-(3,4-Dimethyl-5-isoxazolyl)-2-((4-methylphenyl)-oxy)-benzenesulfonamide

A. N-(3,4-Dimethyl-5-isoxazolyl)-N-[(2-methoxyethoxy)]methyl]-2-((4-methylphenyl)-oxy)-benzenesulfonamide To p-cresol (195 mg, 1.8 mmol) in pyridine (2 mL) at 0° C., sodium hydride (60% in mineral oil, 72 mg, 1.8 mmol) was added. The mixture was stirred at 0° C. for 10 minutes and copper(I) bromide-dimethyl sulfide (432 mg, 2.1 mmol) was added. The mixture was stirred at room temperature for 30 minutes and a solution of compound A from Example 4 (630 mg, 1.5 mmol) in pyridine (2 mL) was added. The mixture was refluxed for 2.5 hours, cooled, diluted with ethyl acetate and filtered. The filtrate was washed twice with saturated aqueous ammonium chloride, dried and concentrated. The residue was chromatographed on silica gel with 4:1 hexane/ethyl acetate to afford compound A as a light yellow gum.

B. N-(3,4-Dimethyl-5-isoxazolyl)-2-((4-methylphenyl)-oxy)-benzenesulfonamide

The title compound was prepared from compound A as described for Example 18, with refluxing for 2.5 hours. Chromatography on silica with 3:1 hexanes:ethyl acetate provided the title compound as a light yellow solid, m.p. 128–131° C.

Analysis calculated for $C_{18}H_{18}N_2O_4S$. Calc'd: C, 60.32; H, 5.06; N, 7.82; S, 8.95. Found: C, 60.59; H, 5.06; N, 7.86; S, 9.16.

EXAMPLE 49

2'-Methylamino-N-(3,4-dimethyl-5-isoxazolyl)-4'-(2-methylpropyl)[1,1'-biphenyl]-2-sulfonamide To a solution of the compound of Example 46 (135 mg, 0.34 mmol), sodium acetate (28 mg, 0.34 mmol) and acetic acid (41 mg, 0.68 mmol) in methanol (3.4 mL), formaldehyde (37% in water, 0.033 mL, 0.41 mmol) and sodium cyanoborohydride (21 mg, 0.34 mmol) were added. The mixture was stirred for 1 hour, concentrated, diluted with ethyl acetate and washed with water and brine, dried and concentrated. The residue was subjected to preparative HPLC on a 30×500 mm ODS S10 column using 56% methanol, 44% water and 0.1% trifluoroacetic acid to provide 23 mg of the title compound (16%) as a white solid, m.p. 125–128° C., as well as 30 mg of the title compound of Example 50 (20%) as a light yellow solid, m.p. 127–129° C.

Analysis calculated for $C_{22}H_{27}N_3O_3S \cdot 0.2H_2O$. Calc'd: C, 63.35; H, 6.62; N, 10.07; S, 7.69. Found: C, 63.45; H, 6.54; N, 9.97; S, 7.35.

EXAMPLE 50

2'-Dimethylamino-N-(3,4-dimethyl-5-isoxazolyl)-4'-(2-methylpropyl)[1,1'-biphenyl]-2-sulfonamide The title compound was prepared from the compound of Example 46 as described under Example 49.

Analysis calculated for $C_{23}H_{29}N_3O_3S$. Calc'd: C, 64.61; H, 6.84; N, 9.83; S, 7.50. Found: C, 64.57; H, 6.90; N, 9.65; S, 7.49.

EXAMPLE 51

3-Methyl-5-[[[4'-(2-methylpropyl)[1,1'-biphenyl]-2-yl]sulfonyl]amino]-4-isoxazolecarboxylic Acid, Ethyl Ester A. N-(1,1-Dimethylethyl)-4'-(2-methylpropyl)-1,1'-biphenyl-2-sulfonamide Compound A was prepared from N-(1,1-dimethylethyl)-2-bromobenzenesulfonamide and compound A from Example 21 as described for compound A from Example 12, using toluene in place of benzene and with heating at reflux for 1 hour. Chromatography on silica gel using 10% hexanes/ethyl acetate afforded compound A as a white solid.

B. 4'-(2-Methylpropyl)-1,1'-biphenyl-2-sulfonamide

Compound A (0.50 g, 1.7 mmol) was added to trifluoroacetic acid (5 mL) at 0° C. and the solution was stirred at room temperature for 5 hours. The solvent was evaporated and the residue was passed through a plug of silica gel using ethyl acetate. The eluate was concentrated to provide compound B as an oil (0.31 g, 100%).

C. 3-Methyl-5-[[[4'-(2-methylpropyl)[1,1'-biphenyl]-2-yl]sulfonyl]amino]-4-isoxazolecarboxylic Acid, Ethyl Ester A mixture of compound B (306 mg, 1.01 mmol), ethyl 5-bromo-3-methyl-4-isoxazolecarboxylate (389 mg, containing 33% of ethyl 4-bromo-3-methyl-5-isoxazolecarboxylate, 1.11 mmol of the correct isomer), and cesium carbonate (658 mg, 2.02 mmol) was heated at 80° C. in dimethylformamide (4 mL) for 2 hours. The solvent was evaporated, the residue was diluted with brine (10 mL), and the pH of the mixture was brought to 2 with 1 N hydrochloric acid. The mixture was extracted with ethyl acetate, the combined organic layers were washed with brine, dried (sodium sulfate) and concentrated. Chromatography (flash, silica, 25, then 50% ethyl acetate/hexanes) yielded a yellow-white solid. This material was dissolved in absolute ethanol (10 mL) and 1 N hydrochloric acid was added to bring the pH of the solution to about 3. The ethanol was evaporated, ether was added to the residue and the solution was washed with water, dried (magnesium sulfate) and evaporated. Recrystallization from ethanol provided the title compound (137 mg, 31%) as fine white needles, mp 133–134° C.

Analysis calculated for $C_{23}H_{26}N_2O_5S \cdot 0.13H_2O$. Calc'd: C, 62.10; H, 5.95; N, 6.30. Found: C, 62.08; H, 5.86; N, 6.46.

EXAMPLE 52

N-(3,4-Dimethyl-5-isoxazolyl)-4'-(cyclopentyl) methyl)[1,1'-biphenyl]-2-sulfonamide A. 4-Bromo-4-(cyclopentylidenemethylenyl)-benzene To a solution of butyllithium in pentane (2 M, 24.3 mL, 48.6 mmol) in 150 mL of ether at 0° C. under argon, was added cyclopentyltriphenylphosphonium bromide (20 g, 48.6 mmol) in portions over 15 minutes. The mixture was stirred for 3 hours as it warmed to room temperature and cooled to −78° C., and then a solution of 4-bromobenzaldehyde (9.4 g, 51 mmol) in 100 mL of ether was added dropwise over 30 minutes. The mixture was stirred for 18 hours as it warmed to room temperature and was filtered, and the solid cake was washed with 200 mL of ether. The combined filtrate was evaporated and the residual solid was chromatographed on silica using hexanes to provide 3.98 g (33%) of compound A.

B. 1-Bromo-4-(cyclopentylmethyl)-benzene

A mixture of compound A (3.8 g, 16 mmol) and $PtO_2$ (150 mg) in ethanol (150 mL) was hydrogenated at 35 psi for 12 minutes. The mixture was filtered and the filtrate was concentrated. The residue was chromatographed on silica gel with hexane to afford 3.22 g of compound B as a colorless liquid (80%).

C. 4-(Cyclopentylmethyl)-benzeneboronic Acid

Compound C was prepared from compound B and trimethylborate as described for compound A from Example 21. Crystallization from ether/hexanes provided compound C as a white solid, mp 189–191° C.

D. N-(3,4-Dimethyl-5-isoxazolyl)-N-[(2-methoxyethoxy)] methyl]-[4'-(cyclopentylmethyl)][1,1'-biphenyl]-2-sulfonamide Compound D was prepared from compound C and compound A from Example 4 as described for compound A from Example 12, using toluene in place of benzene and with heating at reflux for 3 hours. Chromatography on silica gel using 3:1 hexanes/ethyl acetate afforded compound D as a colorless gum.

E. N-(3,4-Dimethyl-5-isoxazolyl)-4'-(cyclopentylmethyl)[1,1'-biphenyl]-2-sulfonamide The title compound was prepared from compound D as described for Example 18, using 6 N hydrochloric acid and with refluxing for 3 hours. Crystallization from hexanes/ethyl acetate afforded the title compound as a white crystalline solid, mp 120–121° C.

Analysis calculated for $C_{23}H_{26}N_2O_3S$. Calc'd: C, 67.29; H, 6.38; N, 6.82; S, 7.81. Found: C, 67.35; H, 6.41; N, 7.05; S, 7.82.

EXAMPLE 53

N-(3,4-Dimethyl-5-isoxazolyl)-2'-(formylamino)-4'-(2-methylpropyl)[1,1'-biphenyl]-2-sulfonamide To a solution of the compound of Example 32 (0.20 g, 0.5 mmol) in toluene (2 mL), formic acid (0.21 g, 4.5 mmol) was added. The mixture was heated at reflux for 3 hours, additional formic acid (0.23 g, 5 mmol) was added and heating was continued for 9 hours. The mixture was concentrated and the residue was chromatographed on silica gel to provide the title compound (127 mg, 59%) as an off-white solid, m.p. 87–95° C.

Analysis calculated for $C_{22}H_{25}N_3O_4S$. Calc'd: C, 61.81; H, 5.89; N, 9.83; S, 7.50. Found: C, 61.68; H, 6.03; N, 9.66; S, 7.45.

EXAMPLE 54

N-(3,4-Dimethyl-5-isoxazolyl)-4'-(cyclopropylmethyl)[1,1'-biphenyl]-2-sulfonamide A. 4-Bromo-4-(cyclopropylidenemethylenyl)-benzene A solution of 4-bromobenzaldehyde (5.36 g, 29.0 mmol) and Tris[2-(2-methoxyethoxy)ethyl]amine (1.22 g, 3.78 mmol) in tetrahydrofuran (40 mL) was added to a suspension of sodium hydride (60% in mineral oil, 1.51 g, 37.7 mmol) and cyclopropylphosphonium bromide (14.4 g, 37.7 mmol) in tetrahydrofuran (120 mL). The resulting suspension was heated at 62° C. for 1.5 hours, cooled and diluted with hexanes (500 mL), and the mixture was passed through a short pad of silica gel. The eluate was concentrated and the residue was chromatographed on silica gel with hexanes to afford 4.0 g of compound A (66%) as a colorless liquid.

B. 1-Bromo-4-(cyclopropylmethyl)-benzene

Compound B was prepared as a colorless liquid from compound A as described for compound B from Example 52.

C. 4-(Cyclopropylmethyl)-benzeneboronic Acid

Compound C was prepared as a white solid from compound B and trimethylborate as described for compound A from Example 21.

D. N-(3,4-Dimethyl-5-isoxazolyl)-N-[(2-methoxyethoxy)] methyl]-[4'-(cyclopropylmethyl)][1,1'-biphenyl]-2-sulfonamide Compound D was prepared from compound C and compound A from Example 4 as described for compound A from Example 12, using toluene in place of benzene and with heating at 80° C. for 2.5 hours. Chromatography on silica gel using 5:1 hexanes/ethyl acetate afforded compound D as a colorless gum.

E. N-(3,4-Dimethyl-5-isoxazolyl)-4'-(cyclopropylmethyl)[1,1'-biphenyl]-2-sulfonamide The title compound was prepared from compound D as described for Example 18, using 6 N hydrochloric acid and with refluxing for 4.5 hours. Chromatography on silica gel with 4:1 hexanes/ethyl acetate followed by preparative HPLC (30×500 mm ODS S10 column using 75% methanol, 25% water and 0.1% TFA) afforded the title compound as a white solid, m.p. 50–54° C.

Analysis calculated for $C_{21}H_{22}N_2O_3S.0.35H_2O$. Calc'd: C, 64.88; H, 5.88; N, 7.21; S, 8.25. Found: C, 64.80; H, 5.57; N, 7.29; S, 8.53.

EXAMPLE 55

N-(3,4-Dimethyl-5-isoxazolyl)-4-methoxy-4'-(2-methylpropyl)[1,1'-biphenyl]-2-sulfonamide A. 2-Bromo-N-(3,4-dimethyl-5-isoxazolyl)-5-methoxybenzenesulfonamide A solution of 2-bromo-5-methoxy-benzenesulfonyl chloride (0.90 g, 3.15 mmol), 3,4-dimethyl-5-isoxazolamine (0.46 g, 4.1 mmol) and dimethylaminopyridine (77 mg, 0.63 mmol) in dry pyridine (6 mL) was heated at 70° C. for 15 hours. Most of the pyridine was evaporated, the residue was poured into saturated sodium bicarbonate (50 mL) and 0.5 N sodium carbonate was added to bring the pH to 9.5. The mixture was washed four times with ether, acidified with 6 N hydrochloric acid to pH 2, and extracted three times with ether. These latter combined organic layers were dried (magnesium sulfate) and concentrated under vacuum to afford compound A.

B. 2-Bromo-N-(3,4-dimethyl-5-isoxazolyl)-5-methoxy-N-[(2-methoxyethoxy)]methyl]-benzenesulfonamide To a suspension at 0° C. of hexanes-degreased sodium hydride (132 mg of 80% oil dispersion, 4.42 mmol) in tetrahydrofuran (25 mL) was added dropwise a solution of compound A (1.35 g, 3.74 mmol) in tetrahydrofuran (20 mL) followed by methoxyethoxymethyl chloride (0.50 mL, 4.4 mmol) dropwise. The mixture was stirred at room temperature for 3 hours, water was added, the tetrahydrofuran was evaporated and the residue was partitioned between ether and water (100 mL, containing 1 mL of 1 N hydrochloric acid). The ether layer was washed with brine, dried (magnesium sulfate) and evaporated. Chromatography (silica, 40% ethyl acetate/hexanes (1 L), then 60% ethyl acetate/hexanes) yielded compound B as a colorless transparent oil.

C. N-(3,4-Dimethyl-5-isoxazolyl)-4-methoxy-N-[(2-methoxyethoxy)]methyl]-4'-(2-methylpropyl)-[1,1'-biphenyl]-2-sulfonamide Compound C was prepared from compound B and compound A from Example 21 as described for compound A from Example 12, using argon degassed solutions, using toluene in place of benzene and with heating at reflux for 3 hours. Chromatography on silica gel using 3:1 hexanes/ethyl acetate afforded compound C as a glass.

D. N-(3,4-Dimethyl-5-isoxazolyl)-4-methoxy-4'-(2-methylpropyl)[1,1'-biphenyl]-2-sulfonamide The title compound was prepared from compound C as described for Example 18, using 6 N hydrochloric acid and with refluxing for 24 hours. Chromatography on silica gel with 3:2 hexanes/ethyl acetate followed by recrystallization from ethyl acetate/hexanes afforded the title compound as a white solid, m.p. 132–134° C.

Analysis calculated for $C_{22}H_{26}N_2O_4S$. Calc'd: C, 63.75; H, 6.32; N, 6.76; S, 7.73. Found: C, 63.91; H, 6.38; N, 7.11; S, 7.76.

EXAMPLE 56

N-(3,4-Dimethyl-5-isoxazolyl)-4'-(2-methylbutyl)-[1,1'-biphenyl]-2-sulfonamide

A. 1-Bromo-4-(2-methyl-but-1-enyl)-benzene

Compound A was prepared from isobutyltriphenylphosphonium bromide and 4-bromo-benzaldehyde as described for compound A from Example 52. Following chromatography on silica using hexanes, distillation (bp 92–100° C. at 25 mm) afforded compound A as a colorless liquid.

B. 1-Bromo-4-(2-methyl-butyl)-benzene

Compound B was prepared as a colorless liquid from compound A as described for compound B from Example 52, with hydrogenation at 30 psi for 12 minutes. After filtration, the filtrate was evaporated and the residual liquid was distilled (bp 92–95° C. at 25 mm) to provide compound B as a colorless liquid.

C. 4-(2-Methyl-butyl)-benzeneboronic Acid

Compound C was prepared as a white solid from compound B and trimethylborate as described for compound A from Example 21. Crystallization from ether/hexanes provided compound C as a white solid, mp 136–138° C.

D. N-(3,4-Dimethyl-5-isoxazolyl)-N-[(2-methoxyethoxy)]methyl]-[4'-(2-methyl-butyl)][1,1'-biphenyl]-2-sulfonamide Compound D was prepared from compound C and compound A from Example 4 as described for compound A from Example 12, using toluene in place of benzene and with heating at reflux for 3 hours. Chromatography on silica gel using 3:1 hexanes/ethyl acetate afforded compound D as a colorless gum.

E. N-(3,4-Dimethyl-5-isoxazolyl)-4'-(2-methylbutyl)-[1,1'-biphenyl]-2-sulfonamide The title compound was prepared from compound D as described for Example 18, using 6 N hydrochloric acid and with refluxing for 3 hours. Crystallization from hexanes/ ethyl acetate afforded the title compound as a white solid, mp 124–125° C.

Analysis calculated for $C_{22}H_{26}N_2O_3S \cdot 1.0H_2O$. Calc'd: C, 63.44; H, 6.77; N, 6.73; S, 7.70. Found: C, 63.44; H, 6.19; N, 6.41; S, 7.55.

EXAMPLE 57

N-(3,4-Dimethyl-5-isoxazolyl)-4'-(1-methylethyl)-[1,1'-biphenyl]-2-sulfonamide

A. 4-(1-Methyl-ethyl)-benzeneboronic Acid

Compound A was prepared as a white solid from 4-isopropyl-bromobenzene and trimethylborate as described for compound A from Example 21. Crystallization from ether/hexanes provided compound A as a white solid, mp 140–141° C.

B. N-(3,4-Dimethyl-5-isoxazolyl)-N-[(2-methoxyethoxy)] methyl]-[4'-(1-methyl-ethyl)][1,1'-biphenyl]-2-sulfonamide Compound B was prepared from compound A and compound A from Example 4 as described for compound A from Example 12, using toluene in place of benzene and with heating at reflux for 3 hours. Chromatography on silica gel using 3:1 hexanes/ethyl acetate afforded compound B as a colorless gum.

C. N-(3,4-Dimethyl-5-isoxazolyl)-4'-(1-methylethyl)-[1,1'-biphenyl]-2-sulfonamide The title compound was prepared from compound B as described for Example 18, using 6 N hydrochloric acid and with refluxing for 3 hours. Crystallization from hexanes/ ethyl acetate afforded the title compound as a white solid, mp 162–163° C.

Analysis calculated for $C_{20}H_{22}N_2O_3S \cdot 0.30H_2O$. Calc'd, C, 63.92; H, 6.06; N, 7.45; S, 8.53. Found: C, 63.93; H, 5.80; N, 7.44; S, 8.69.

EXAMPLE 58

N-(3,4-Dimethyl-5-isoxazolyl)-2'-ethylamino-4'-(2-methylpropyl)-[1,1'-biphenyl]-2-sulfonamide To a solution of the compound of Example 32 (0.16 g, 0.4 mmol) and acetic acid (0.06 g, 1 mmol) in dichloroethane (2.5 mL) at 0° C., acetaldehyde (24 mg, 0.55 mmol) and sodium triacetoxyborohydride (212 mg, 1 mmol) were added. The mixture was stirred at 0–15° C. for 2 hours, diluted with ethyl acetate, extracted with water and brine, dried and concentrated. The residue was chromatographed on silica gel with 4:1 hexanes/ethyl acetate to afford the title compound (90 mg, 53%) as a light yellow gum.

Analysis calculated for $C_{23}H_{29}N_3O_3S \cdot 0.2H_2O$. Calc'd: C, 64.07; H, 6.87; N, 9.75; S, 7.44. Found: C, 64.23; H, 6.49; N, 9.57; S, 7.31.

EXAMPLE 59

N-[2-[[(3,4-Dimethyl-5-isoxazolyl)amino]sulfonyl]-4'-(2-methylpropyl)[1,1'-biphenyl]-5-yl]benzamide To a solution of the compound of Example 43 (0.4 g, 1.0 mmol) and pyridine (0.082 mL, 1.0 mmol) in acetone (3 mL) was added benzoyl chloride (0.12 mL, 1.0 mmol). The mixture was stirred for 18 hours and concentrated. The residue was dissolved in methanol (50 mL) and a 5% solution of sodium hydrogen carbonate in water (10 mL) was added. The solution was stirred for 1 hour and the methanol was removed under vacuum. The aqueous residue was acidified to pH 3 with 6N aqueous hydrochloric acid and extracted three times with ethyl acetate. The combined organic phases were washed with water and brine, and dried (magnesium sulfate). The residue was chromatographed on silica with (1:1) ethyl acetate:hexanes to afford 98 mg (19%) of the title compound as a tan solid, mp 207–211° C.

Analysis calculated for $C_{28}H_{29}N_3O_4S \cdot 1.15H_2O$. Calc'd: C, 64.14; H, 6.02; N, 8.01; S, 6.11. Found: C, 64.36; H, 5.75; N, 7.79; S, 5.84.

EXAMPLE 60

N-(3,4-Dimethyl-5-isoxazolyl)-4-hydroxy-4'-(2-methylpropyl)[1,1'-biphenyl]-2-sulfonamide To a solution at −78° C. of the compound of Example 55 (202 mg, 0.49 mmol) in dry methylene chloride (5 mL) was added dropwise a solution of boron tribromide (1M in methylene chloride, 3.9 mL, 3.9 mmol). The solution was stirred for 18 hours at room temperature and diluted with methylene chloride (50 mL). Ice (5 g) was added and the pH of the resulting aqueous layer was brought to 0–1 with saturated sodium hydrogen carbonate solution. The organic layer was separated, the aqueous layer was extracted with methylene chloride and the combined organic layers were dried (magnesium sulfate) and evaporated. Chromatography (silica, 50% ethyl acetate/hexanes) provided a white foam which was recrystallized from ethyl acetate/hexanes to provide 167 mg (86%) of the title compound as white crystals, mp 159–160° C.

Analysis calculated for $C_{21}H_{24}N_2O_4S \cdot 0.62H_2O$. Calc'd: C, 56.09; H, 5.37; N, 12.26; S, 9.36. Found: C, 56.23; H, 5.34; N, 12.12; S, 9.27.

EXAMPLE 61

[N-[2'-[[(3,4-Dimethyl-5-isoxazolyl)amino]sulfonyl]-4-(2-methylpropyl)[1,1'-biphenyl]-2-yl]amino]acetic Acid The title compound was prepared from Example 32 and glyoxylic acid monohydrate as described for Example 58, using methanol as solvent and with stirring at room temperature for 90 minutes. Following workup, crystallization from methylene chloride/hexanes provided the title compound as white crystals, mp 147–150° C.

Analysis calculated for $C_{23}H_{27}N_3O_5S \cdot 0.8H_2O$. Calc'd: C, 58.53; H, 6.11; N, 8.90; S, 6.79. Found: C, 58.52; H, 5.94; N, 8.94; S, 6.57.

EXAMPLE 62

N-[2-[[(3,4-Dimethyl-5-isoxazolyl)amino]sulfonyl]-4'-(2-methylpropyl)[1,1'-biphenyl]-5-yl]acetamide The title compound was prepared from Example 43 and acetyl chloride as described for Example 59, with stirring for 3.5 hours. Chromatography on silica (1:1 ethyl acetate:hexanes) followed by trituration with warm hexanes afforded the title compound as a tan solid, mp 150–154° C.

Analysis calculated for $C_{23}H_{27}N_3O_4S \cdot 0.95H_2O$. Calc'd: C, 60.24; H, 6.35; N, 9.16; S, 6.99. Found: C, 60.57; H, 5.94; N, 8.83; S, 6.68.

EXAMPLE 63

N-(3,4-Dimethyl-5-isoxazolyl)-4'-(2-methyl-1-propenyl)[1,1'-biphenyl]-2-sulfonamide A. 4-(2-Methyl-1-propenyl)benzeneboronic Acid n-Butyllithium (2.5 M in hexane, 3.2 mL, 8.0 mmol) was added over 5 minutes to a solution of 4-(2-methyl-1-propenyl)bromobenzene (1.7 g, 8.0 mmol) in tetrahydrofuran (8.6 mL) and ether (26 mL) stirring at −78° C. under argon. After stirring at −78° C. for 50 min, this solution was transferred via cannula over 5 minutes to a solution of triisopropylborate (3.1 g, 16 mmol) in ether (17 mL) stirring at −78° C. After stirring at −78° C. for 1.5 hours and at ambient temperature for 25 minutes, the reaction was quenched with 1N HCl (50 ml) and allowed to stir for 30 minutes. The solution was extracted twice with ether and the combined organic layers were extracted three times with 1N NaOH. The combined aqueous layers were acidified with 6N HCl to pH 1 and extracted three times with ether. Washing the last three ether extracts with brine and drying over magnesium sulfate afforded 1.2 g (79%) of compound A after evaporation of the solvent.

B. N-(3,4-Dimethyl-5-isoxazolyl)-N-[(2-methoxyethoxy)methyl]-4'-(2-methyl-1-propenyl)[1,1'-biphenyl]-2-sulfonamide Compound B was prepared from compound A and compound A from Example 4 as described for compound A from Example 12, using argon degassed solutions, using toluene in place of benzene and with heating at reflux for 1 hour. Flash chromatography on silica gel using 4:1 hexanes/ethyl acetate afforded compound B.

C. N-(3,4-Dimethyl-5-isoxazoyl)-4'-(2-methyl-1-propenyl)-[1,1'-biphenyl]-2-sulfonamide The title compound was prepared from compound B as described for Example 18, using 6 N hydrochloric acid and with heating at 80° C. for 2 hours. Two flash chromatographies (10% ethyl acetate/methylene chloride followed by 10% acetone/hexane) followed by preparative HPLC (YMC SH 345-15 S-15 120 A, 20 mm×500 mm, 25 ml/min, A=$H_2O$+0.1% TFA, B=$CH_3CN$+0.1% TFA; 43% A to 30% A over 45 min: $t_R$=29 min) afforded the title compound as a white solid, mp 58–63° C.

Analysis calculated for $C_{21}H_{22}N_2O_3S \cdot 0.30H_2O$. Calc'd: C, 65.02; H, 5.87; N, 7.22; S, 8.26. Found: C, 65.09; H, 5.78; N, 7.15; S, 8.20.

EXAMPLE 64

N-(3,4-Dimethyl-5-isoxazolyl)-4'-(2-methylpropyl)-2'-(propylamino)-[1,1'-biphenyl]-2-sulfonamide The title compound was prepared from the compound of Example 32 and propionaldehyde as described for Example 58, with stirring at 0–5° C. for 2 hours. Following workup, chromatography on silica gel with 4:1 hexanes/ethyl acetate afforded the title compound as a light yellow gum.

$^1$H NMR (CDCl$_3$): δ 0.86 (t, J=6 Hz, 3H), 0.95 (d, J=6 Hz, 6H), 1.50 (m, 2H), 1.92 (s, 3H), 1.93 (m, 1H), 2.17 (s, 3H), 2.49 (d, J=7 Hz, 2H), 3.02 (t, J=6 Hz, 2H), 6.61–7.90 (m, 7H). Analysis calculated for $C_{24}H_{31}N_3O_3S \cdot 0.28H_2O$. Calc'd: C, 64.54; H, 7.12; N, 9.41; S, 7.18. Found: C, 64.58; H, 6.89; N, 9.37; S, 6.75.

EXAMPLE 65

N-(3,4-Dimethyl-5-isoxazolyl)-2'-(1-methyl-(ethylamino))-4'-(2-methylpropyl)-[1,1'-biphenyl]-2-sulfonamide The title compound was prepared from the compound of Example 32 and acetone as described for Example 58, with stirring at room temperature for 3 hours. Workup afforded the title compound as a light yellow gum.

$^1$H NMR (CDCl$_3$): δ 0.93 (d, J=6 Hz, 6H), 1.03 (d, J=6 Hz, 3H), 1.10 (d, J=6 Hz, 3H), 1.90 (m, 1H), 1.91 (s, 3H), 2.16 (s, 3H), 2.48 (d, J=7 Hz, 2H), 3.58 (m, 1H), 6.61–7.87

(m, 7H). Analysis calculated for $C_{24}H_{31}N_3O_3S \cdot 0.16H_2O$. Calc'd: C, 64.86; H, 7.10; N, 9.46; S, 7.21. Found: C, 64.97; H, 7.03; N, 9.35; S, 7.25.

EXAMPLE 66

N-(3,4-Dimethyl-5-isoxazolyl)-2'-(2-hydroxy-(ethylamino))-4'-(2-methylpropyl)-[1,1'-biphenyl]-2-sulfonamide The title compound was prepared from the compound of Example 32 and glycolaldehyde dimer as described for Example 58, with stirring at room temperature for 2 hours. Following workup, chromatography on silica gel with 4:1 methylene chloride/ethyl acetate afforded the title compound as a white solid, mp 45–53° C.

Analysis calculated for $C_{23}H_{29}N_3O_4S \cdot 0.15H_2O$. Calc'd: C, 61.90; H, 6.62; N, 9.41; S, 7.18. Found: C, 62.05; H, 6.59; N, 9.26; S, 6.94.

EXAMPLE 67

N-(3,4-Dimethyl-5-isoxazolyl)-4'-(2-methylpropyl)-5-[(2-phenylethyl)amino]-[1,1'-biphenyl]-2-sulfonamide A. N-[2-[[(3,4-Dimethyl-5-isoxazolyl)-amino]sulfonyl]-4'-(2-methylpropyl)[1,1'-biphenyl]-5-yl]phenylacetamide Compound A was prepared from the compound of Example 43 and phenylacetylchloride as described for Example 59.

B. N-(3,4-Dimethyl-5-isoxazolyl)-4'-(2-methylpropyl)-5-[(2-phenylethyl)amino]-[1,1'-biphenyl]-2-sulfonamide To a solution of compound A (180 mg, 0.35 mmol) in dry tetrahydrofuran (4 mL) was added borane-methyl sulfide complex (0.14 mL, 1.39 mmole) dropwise at 0° C. The mixture was stirred at 0° C. for 15 minutes, warmed to room temperature over 15 minutes, heated at reflux for 3 hours, and cooled to 0° C. Methanol (3 mL) was added, the mixture was stirred for 40 minutes and concentrated hydrochloric acid was added to adjust the pH to 2. The mixture was heated to reflux for 40 minutes, cooled to room temperature and concentrated. The residue was slurried in water and the pH was adjusted to 3 with 5% sodium bicarbonate. The solid was collected, rinsed with water, and dried to afford a tan solid. The mixture was chromatographed on silica with ethyl acetate:hexanes (1:1) and the product was triturated with hexanes to afford 34 mg (19%) of the title compound as a white amorphous solid, mp 68–71° C.

Analysis calculated for $C_{29}H_{33}N_3O_3S \cdot 0.59H_2O$. Calc'd: C, 67.74; H, 6.70; N, 8.17; S, 6.23. Found: C, 67.77; H, 6.58; N, 8.14; S, 6.27.

EXAMPLE 68

N-(3,4-Dimethyl-5-isoxazolyl)-4'-(2-methylpropyl)-5-[(2-methylpropyl)amino]-[1,1'-biphenyl]-2-sulfonamide A. N-[2-[[(3,4-Dimethyl-5-isoxazolyl)amino]-sulfonyl]-4'-(2-methylpropyl)[1,1'-biphenyl]-5-yl]-(2-methylpropionamide)

Compound A was prepared from the compound of Example 43 and isobutyrylchloride as described for Example 59, with stirring for 3 hours.

B. N-(3,4-Dimethyl-5-isoxazolyl)-4'-(2-methylpropyl)-5-[(2-methylpropyl)amino]-[1,1'-biphenyl]-2-sulfonamide The title compound was prepared from Compound A as described for Example 67. Chromatography on silica with 1:1 ethyl acetate:hexanes followed by trituration with hexanes afforded the title compound as a tan amorphous solid, mp 74–78° C.

Analysis calculated for $C_{25}H_{33}N_3O_3S \cdot 0.45H_2O \cdot 0.1CHCl_3$. Calc'd: C, 63.38; H, 7.20; N, 8.83; S, 6.73. Found: C, 63.18; H, 6.81; N, 8.95; S, 6.94.

EXAMPLE 69

N-(3,4-Dimethyl-5-isoxazolyl)-4'-(2,2-dimethylpropyl)-[1,1'-biphenyl]-2-sulfonamide A. 4'-Bromomethyl-N-(3,4-dimethyl-5-isoxazolyl)-N-(methoxyethoxymethyl)[1,1'-biphenyl]-2-sulfonamide To a solution of Compound A from Example 11 (7.7 g, 18 mmol) in carbon tetrachloride (180 mL), N-bromosuccinimide (4.14 g, 23.2 mmol) and benzoyl peroxide (385 mg, 1.59 mmol) were added. The mixture was refluxed for 1.5 hours, cooled, diluted with 200 mL of methylene chloride, extracted twice with water, extracted once with brine, dried and concentrated. The residue was chromatographed on silica gel with 4:1 hexanes/ethyl acetate to provide compound A (3.64 g, 40%) as a colorless gum.

B. N-(3,4-Dimethyl-5-isoxazolyl)-N-[(2-methoxyethoxy)]methyl]-[4'-(2,2-dimethylpropyl)]-[1,1-biphenyl]-2-sulfonamide To a solution of benzenethiol-tert-butylcopper lithium complex (8.5 mmol) in tetrahydrofuran (25 mL) (prepared as described in *Organic Syntheses*, vol. 6, p. 248) at −65° C., a solution of compound A (1.45 g, 2.84 mmol) in tetrahydrofuran (5.7 mL) was added dropwise. The mixture was stirred at −60° C. to −65° C. for 30 minutes and saturated ammonium chloride was added. The mixture was diluted with ethyl acetate, washed twice with brine, dried and concentrated. The residue was chromatographed on silica gel using 7:1 hexanes/ethyl acetate to afford compound B (181 mg, 13%) as a colorless gum.

C. N-(3,4-Dimethyl-5-isoxazolyl)-4'-(2,2-dimethylpropyl)-[1,1'-biphenyl]-2-sulfonamide The title compound was prepared from compound B as described for Example 18, using 3 N hydrochloric acid and with refluxing for 5 hours. Chromatography on silica with 3:1 hexanes/ethyl acetate afforded the title compound as a white solid, m.p. 54–57° C.

Analysis calculated for $C_{22}H_{26}N_2O_3S \cdot 0.3H_2O$. Calc'd: C, 65.43; H, 6.64; N, 6.94; S, 7.94. Found: C, 65.47; H, 6.53; N, 6.90; S, 8.05.

EXAMPLE 70

N-(3,4-Dimethyl-5-isoxazolyl)-4'-(2-methylpropyl)-4-[(phenylmethyl)oxyl-[1,1'-biphenyl]-2-sulfonamide A. Sodium 3-(Phenylmethoxy)benzenesulfonate A solution of 3-hydroxybenzene sulfonate (10.0 g, 57.4 mmol) in water (80 mL) was adjusted to pH 12 with 5 N NaOH. Benzyl bromide (7.2 mL, 60 mmol) was added dropwise to the vigorously stirred solution. After stirring for 18 hours, about 50 mL of the water was evaporated. The residue was chilled to 4° C. and the precipitate was collected by filtration, washed twice with ice water and dried to provide compound A as a white solid (11.2 g, 68%).

B. 2-Bromo-5-(phenylmethoxy)benzenesulfonyl Chloride

A solution of bromine (2.24 g, 14.0 mmol) in water (60 mL) was added dropwise to a stirred solution of compound A (4.0 g, 14 mmol) in water (25 mL) and tetrahydrofuran (15 mL) at 0° C. After stirring for 2 hours, the pH of the reaction was brought to 8.5 with 0.5 N sodium carbonate, excess bromine was discharged with sodium bisulfite and the reaction was evaporated to provide a solid. To this solid was added phosphorus pentachloride (5.82 g, 27.9 mmol). An exotherm ensued, the mixture liquified and the mixture was heated at 50° C. for 1 hour and cooled to room temperature. The resultant paste was mixed with crushed ice (20 g), the mixture was diluted with water and extracted twice with ether. The combined organic layers were dried (sodium sulfate) and concentrated to afford a brown solid (4 g).

C. N-(3,4-Dimethyl-5-isoxazolyl)-2-bromo-5-(phenylmethoxy)benzenesulfonamide

A solution of compound B, 3,4-dimethylisoxazolamine (1.6 g, 14 mmol) and dimethylaminopyridine (0.27 g, 2.2 mmol) in pyridine (10 mL) was stirred for 2 hours and evaporated. The residue was partitioned between ether (250 mL) and 0.5 N HCl (250 mL). A dark oil formed. The aqueous layer was extracted with ether (2×100 mL). The combined organic layers were washed with 0.5 N HCl (2×50 mL). The acid washings and original acid layer were combined with the dark oil and the whole was extracted with methylene chloride (2×100 mL). The methylene chloride and ether extracts were dried (sodium sulfate) and concentrated. Chromatography (silica, 50% ethyl acetate/hexanes) provided 361 mg (7%) of compound C as a foam.

D. N-(3,4-Dimethyl-5-isoxazolyl)-N-((2-methoxyethoxy)methyl)-2-bromo-5-(phenylmethoxy)benzenesulfonamide Compound D was prepared as a yellow oil from compound C as described for compound B of Example 55.

E. N-(3,4-Dimethyl-5-isoxazolyl)-N-((2-methoxyethoxy)methyl)-4'-(2-methylpropyl)-4-(phenylmethoxy)[1,1'-biphenyl]-2-sulfonamide Compound E was prepared from compound D and 4-isobutylbenzene boronic acid as described for compound A from Example 12, using toluene in place of benzene and with heating at reflux for 3 hours. Chromatography on silica gel using 3:1 hexanes/ethyl acetate afforded compound E as a transparent off-white oil.

F. N-(3,4-Dimethyl-5-isoxazolyl)-4'-(2-methylpropyl)-4-(phenylmethoxy)[1,1'-biphenyl]-2-sulfonamide To a warm solution of compound E in ethanol (15 mL) was added concentrated hydrochloric acid (5 mL). The mixture was heated to reflux for 7 hours and most of the ethanol was evaporated. The residue was partitioned between saturated sodium chloride and ether, the aqueous layer was extracted with ether and the combined organic layers were dried (magnesium sulfate) and concentrated. Chromatography (silica, 25% ethyl acetate/hexanes) and subsequent recrystallization (hexanes (15 mL) containing a trace of ether) yielded the title compound as a white powder, mp 96–101° C.

Analysis calculated for $C_{28}H_{30}N_2O_4S.0.17H_2O$. Calc'd: C, 68.11; H, 6.20; N, 5.67; S, 6.49. Found: C, 68.13; H, 6.18; N, 5.52; S, 6.44.

EXAMPLE 71

N-(3,4-Dimethyl-5-isoxazolyl)-2'-[[(methylamino)carbonyl]amino]-4'-(2-methylpropyl)[1,1'-biphenyl]-2-sulfonamide To a solution of the compound of Example 32 (50 mg, 0.12 mmol) in 1.3 mL of methylene chloride at 0° C., methyl isocyanate (71 mg, 1.2 mmol) was added. The reaction was stirred at room temperature for 3 hours and concentrated. The residue was crystallized from methylene chloride/hexanes to afford 57 mg (100%) of the title compound as a white crystalline solid, m.p. 172–174° C.

Analysis calculated for $C_{23}H_{28}N_4O_4S.0.49H_2O$. Calc'd: C, 59.36; H, 6.28; N, 12.04; S, 6.89. Found: C, 59.44; H, 6.02; N, 11.96; S, 6.98.

EXAMPLE 72

N-(3,4-Dimethyl-5-isoxazolyl)-4'-(2-methylpropyl)-4-[(2-phenylethyl)oxy]-[1,1-biphenyl]-2-sulfonamide A. 3-(2-Phenylethoxy)benzenesulfonic Acid A mixture of 3-hydroxybenzene sulfonic acid (1.4 g, 8.3 mmol), 2-phenylethyl bromide (2.4 mL, 17 mmol) and 2 N sodium hydroxide (12 mL) in isopropanol (40 mL) was refluxed for 3 days. The propanol was evaporated and the residue was washed with ethyl acetate, acidified with HCl, and extracted with ethyl acetate. The latter extracts were dried and evaporated to provide compound A (1.5 g, 64%).

B. 2-Bromo-5-(2-phenylethoxy)benzenesulfonyl Chloride

Compound B was prepared from the sodium salt of compound A as described for compound B of example 70. Silica gel chromatography using 10% ethyl acetate/hexanes afforded pure compound B.

C. N-(3,4-Dimethyl-5-isoxazolyl)-2-bromo-5-(2-phenylethoxy)benzenesulfonamide

A solution of compound B (1.4 g, 3.7 mmol), 3,4-dimethylisoxazolamine (0.54 g, 4.8 mmol) and dimethylaminopyridine (0.09 g, 0.7 mmol) in pyridine (7 mL) was stirred for 1 hour at 70° C. The mixture was diluted with water, acidified with 6 N HCl and extracted twice with ethyl acetate. The extracts were washed with saturated sodium chloride, dried (magnesium sulfate) and concentrated. Chromatography (silica, 10% methanol/dichloromethane) provided 0.2 g (12%) of compound C.

D. N-(3,4-Dimethyl-5-isoxazolyl)-N-((2-methoxy-ethoxy)methyl)-2-bromo-5-(2-phenylethoxy)benzenesulfonamide Compound D was prepared in 76% yield from compound C as described for compound B of Example 55.

E. N-(3,4-Dimethyl-5-isoxazolyl)-N-((2-methoxy-ethoxy)methyl)-4'-(2-methylpropyl)-4-(2-phenylethoxy)-[1,1'-biphenyl]-2-sulfonamide Compound E was prepared from compound D and 4-isobutylbenzene boronic acid as described for compound A from Example 12, using toluene in place of benzene and with heating at reflux for 2 hours. Chromatography on silica gel using 5% ethyl acetate/dichloromethane afforded compound E in 79% yield.

F. N-(3,4-Dimethyl-5-isoxazolyl)-4'-(2-methylpropyl)-4-(2-phenylethoxy)[1,1'-biphenyl]-2-sulfonamide A mixture of compound E in ethanol (2.5 mL) and 6 N HCl (2.5 mL) was heated to reflux for 3 days and most of the ethanol was evaporated. The residue was partitioned between water and dichloromethane. The organic layer was dried (magnesium sulfate) and concentrated. Chromatography (silica, 30% ethyl acetate/hexanes) yielded the title compound as an oil (Rf, silica, 5% ethyl acetate/dichloromethane, 0.79).

Analysis calculated for $C_{29}H_{32}N_2O_4S.0.8H_2O$. Calc'd: C, 67.11; H, 6.52; N, 5.40; S, 6.18. Found: C, 67.48; H, 6.18; N, 5.03; S, 6.07.

EXAMPLE 73

5-[(Carboxymethyl)amino]-N-(3,4-dimethyl-5-isoxazolyl)-4'-(2-methylpropyl)[1,1'-biphenyl]-2-sulfonamide To a solution of the compound of Example 43 (0.19 g, 0.47 mmol) and glyoxylic acid monohydrate (56.0 mg, 0.61 mmol) in methanol (5 mL) at 0° C. was added glacial acetic acid (0.054 mL, 0.94 mmol) and sodium triacetoxyborohydride (0.30 g, 1.4 mmol). The mixture was warmed to room temperature and stirred for 18 hours. Additional amounts of glacial acetic acid (0.054 mL, 0.94 mmol) and sodium triacetoxyborohydride (0.30 g, 1.4 mmol) were added and the reaction was stirred for 48 hours and poured into water (50 mL). The precipitate was collected, rinsed with water, and dried under vacuum. The residue was dissolved in 2 mL of ethyl acetate and applied to four silica gel thick plates which were eluted with (2:1) hexanes/ethyl acetate. The appropriate bands were cut, extracted with ethyl acetate and the enriched product was triturated with hexanes three times followed by precipitation twice from ethyl acetate with hexanes. Drying at 160 torr at 35° C. for three days afforded 3.5 mg of the title compound as a yellow amorphous solid, m.p. 73–78° C.

(M+H)$^+$458; Analysis calculated for $C_{23}H_{27}N_3O_5S$-0.4$C_6H_{14}$-0.6$CH_3CO_2H$-0.2$CHCl_3$. Calc'd: C, 59.13; H, 6.66; N, 7.38. Found: C, 59.11; H, 6.52; N, 6.96.

EXAMPLE 74

5-[(Aminoacetyl)amino]-N-(3,4-dimethyl-5-isoxazolyl)-4'-(2-methylpropyl)[1,1'-biphenyl]-2-sulfonamide A. 5-[[2-(1,1-Dimethylethoxycarbonylamino)-1-oxoethyl]amino]-N-(3,4-dimethyl-5-isoxazolyl)-4'-(2-methylpropyl)[1,1'-biphenyl]-2-sulfonamide To a solution at 0° C. of Boc-glycine (0.14 g, 0.83 mmol) and triethylamine (0.12 mL, 0.83 mmol) in dry tetrahydrofuran (2.7 mL) was added a 2 M solution of oxalyl chloride in dichloromethane (0.43 mL, 0.87 mmol) followed by dimethylformamide (3 drops). The mixture was stirred at 0° C. for 1 hour, a solution of the compound of Example 43 (0.30 g, 0.75 mmol) and pyridine (0.67 mL, 0.83 mmol) in acetone (3 mL) was added, and the mixture was stirred at room temperature for 18 hours and concentrated. The residue was dissolved in methanol (50 mL) and a 5% solution of sodium hydrogen carbonate in water (10 mL) was added. The solution was stirred for 20 minutes, and concentrated to remove methanol, and the aqueous layer was acidified to pH 3 with 6N aqueous HCl. The mixture was extracted with ethyl acetate, and the organic phase was washed with brine, dried (magnesium sulfate) and evaporated. Chromatography on silica with 1:1 ethyl acetate/hexanes afforded 147 mg of compound A. MS: (M+H)$^+$=557.

B. 5-[(Aminoacetyl)amino]-N-(3,4-dimethyl-5-isoxazolyl)-4'-(2-methylpropyl)[1,1'-biphenyl]-2-sulfonamide Compound A (0.15 g, 0.26 mmol) was dissolved in 97% formic acid (15 mL) at 0° C. and concentrated HCl (1.5 mL) was added. The mixture was stirred at 0° C. for 25 minutes and concentrated, and the residue was chased three times with methanol. The resulting tan solid was triturated with ether/hexanes, dissolved in methanol and precipitated with ether. The solid was dissolved in water and subjected to preparative HPLC on a YMC-S-343 S-10 ODS column (30×500 mm) using a gradient system from 70% water:30% acetonitrile:0.1% TFA to 60% water:40% acetonitrle:0.1% TFA over 45 minutes at 40 mL/min. Appropriate fractions were pooled and lyophilized from water to afford 25 mg (14.5%) of the title compound as a fluffy white lyophilate, m.p. 135–138° C.

Analysis calculated for $C_{23}H_{28}N_4O_4S$-1.45$H_2O$-1.5$CF_3CO_2H$. Calc'd: C, 47.77; H, 4.99; N, 8.57; S, 4.90. Found: C, 47.77; H, 4.91; N, 8.26; S, 4.97.

EXAMPLE 75

N-(3,4-Dimethyl-5-isoxazolyl)-2'-formyl-4'-(2-methylpropyl)[1,1'-biphenyl]-2-sulfonamide A. 3-(2-Methylpropyl)-benzyl Alcohol To a solution of isobutylene (4.4 g, 78 mmol) in 11 mL of tetrahydrofuran at −78° C., 9-BBN (0.5 M in tetrahydrofuran, 157 ml, 78 mmol) was added. The mixture was stirred at −78° C. for 3 hours, warmed to room temperature and stirred overnight. In a separate flask containing 3-bromobenzylalcohol (13.3 g, 71.3 mmol) in 36 mL of tetrahydrofuran, tetrakis(triphenylphosphine)palladium(0) (2.47 g, 2.14 mmol) and 60 mL of 3 M sodium hydroxide were added. The 9-isobutyl-BBN was transferred quickly into the flask under argon and the mixture was refluxed for 21 hours. After cooling with an ice bath, 18 mL of 30% hydrogen peroxide was added slowly, the mixture was stirred for 30 minutes, concentrated to about 100 mL and partitioned between water and ethyl acetate. The aqueous phase was extracted with ethyl acetate. The combined organic extracts were washed with brine, dried and concentrated. The residue was chromatographed on silica gel using 9:1 hexanes/ethyl acetate to afford compound A (8.16 g, 70%) as a liquid.

B. 1,3-Dihydro-1-hydroxy-5-(2-methylpropyl)-2,1-benzoxaborole

Compound B was prepared as a light yellow solid from compound A as described for compound A of Example 38, except that the addition of trimethyl borate was performed at −40° C. and extractions were performed with ethyl acetate, m.p. 96–100° C.

C. N-(3,4-Dimethyl-5-isoxazolyl)-N-[(2-methoxy-ethoxy)]methyl]-[2'-hydroxymethyl-4'-(2-methylpropyl)][1,1'-biphenyl]-2-sulfonamide Compound C was prepared from compound B and compound A from Example 4 as described for compound A from Example 12, using toluene in place of benzene and with heating at 80° C. for 4 hours. Chromatography on silica gel using 2.5:1 hexanes/ethyl acetate afforded compound C as a colorless gum.

D. N-(3,4-Dimethyl-5-isoxazolyl)-N-[(2-methoxy-ethoxy)]methyl]-[2'-formyl-4'-(2-methylpropyl)]-[1,1'-biphenyl]-2-sulfonamide To oxalyl chloride (2 M in methylene chloride, 9 mL, 18 mmol) in 26 mL of methylene chloride at −78° C., a solution of dimethylsulfoxide (2.8 g, 36 mmol) in 39 mL of methylene chloride was added. The solution was stirred for 10 minutes and compound C (2.4 g, 4.8 mmol) in 39 mL of methylene chloride was added and the mixture was stirred at −78° C. for 2 hours. Triethylamine (6.1 g, 60 mmol) was added and the mixture was stirred at −78° C. for 5 minutes and warmed to room temperature over 15 minutes. The mixture was partitioned between 0.5 N HCl and methylene chloride, the aqueous phase was extracted with methylene chloride, the combined organic extracts were dried and concentrated and the residue was chromatographed on silica gel using 3.5:1 hexanes/ethyl acetate to afford compound D (1.83 g, 77%).

E. N-(3,4-Dimethyl-5-isoxazolyl)-2'-formyl-4'-(2-methylpropyl)[1,1'-biphenyl]-2-sulfonamide The title compound was prepared from compound D as described for Example 18, using 6 N hydrochloric acid and with refluxing for 1.5 hours. Chromatography on silica gel using 2.5:1 hexanes/ethyl acetate provided the title compound as an amorphous white solid, m.p. 60–66° C.

Analysis calculated for $C_{22}H_{24}N_2O_4S$.0.28$H_2O$. Calc'd: C, 63.28; H, 5.93; N, 6.71; S, 7.68. Found: C, 63.26; H, 6.09; N, 6.73; S, 7.49.

EXAMPLE 76

2'-[[(3,4-Dimethyl-5-isoxazolyl)amino]sulfonyl]-4-(2-methylpropyl)[1,1'-biphenyl]-2-carboxylic Acid To a solution of the compound Example 75 (103 mg, 0.25 mmol) and sulfamic acid (48 mg, 0.5 mmol) in 2.5 mL THF at −10° C., a solution at 0° C. of sodium chlorite (45 mg, 0.5 mmol) in 2.5 mL of water was added. The mixture was stirred for 5 minutes, 45 mL of methylene chloride was added and the organic phase was separated, washed with water (1 mL), dried and concentrated. The residue was purified by preparative HPLC on a 30×500 mm ODS S10 column (68% methanol, 32% water, 0.1%TFA) to provide the title compound (32 mg, 30%) as a white solid, m.p. >185° C., dec.

Analysis calculated for $C_{22}H_{24}N_2O_5S \cdot 0.50H_2O$. Calc'd: C, 60.39; H, 5.76; N, 6.40; S, 7.33. Found: C, 60.49; H, 5.64; N, 6.30; S, 7.38.

What is claimed is:

1. A pharmaceutical composition comprising at least one endothelin antagonist in combination with at least one additional therapeutic agent selected from ECE inhibitors, PAF antagonists, AII receptor antagonists, renin inhibitors, ACE inhibitors, NEP inhibitors, HMG CoA reductase inhibitors, squalene synthetase inhibitors, bile acid sequestrants, calcium channel blockers, potassium channel activators, beta-adrenergic agents, antiarrhythmic agents, diuretics, and thrombolytic agents wherein said endothelin antagonist is selected from compounds of formula I

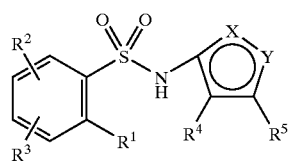

wherein:
one of X and Y is N and the other is O;
$R^1$, $R^2$ and $R^3$ are each independently
  (a) hydrogen, except that $R^1$ is other than hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7 R^8$; or
  (k) —$Z^4$—N($R^{11}$)—$Z^5$—N$R^9 R^{10}$;
  wherein at least one of $R^1$, $R^2$ or $R^3$ is phenyl or biphenyl which may be substituted with $Z^1$, $Z^2$ and $Z^3$;
$R^4$ and $R^5$ are each independently
  (a) hydogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^6$;
  (h) —CO$_2$H or —CO$_2R^6$;
  (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
  (j) —$Z^4$—N$R^7 R^8$; or
  (k) —$Z^4$—N($R^{11}$)—$Z^5$—N$R^9 R^{10}$; or
  (l) $R^4$ and $R^5$ together are alkylene or alkenylene, either of which may be substituted with $Z^1$, $Z^2$ and $Z^3$, completing a 4- to 8-membered saturated, unsaturated or aromatic ring together with the carbon atoms to which they are attached;
$R^6$ is alkyl, alkenyl, alkynyl, alkoxy, cycloalkyl, cycloalkyalkyl, cycloalkenyl, cycloalkenylalkyl, aryl or aralkyl, any of which may be substituted with $Z^1$, $Z^2$ and $Z^3$;
$R^7$ is
  (a) hydrogen;
  (b) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
  (c) cyano;
  (d) hydroxyl;
  (e) —C(O)H or —C(O)$R^6$;
  (f) —CO$_2R^6$; or
  (g) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$, except when $Z^4$ is —S(O)$_n$—;
$R^8$ is
  (a) hydrogen;
  (b) —C(O)H or —C(O)$R^6$, except when $Z^4$ is —C(O)— and $R^7$ is —C(O)H, —C(O)$R^6$ or —CO$_2R^6$; or
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$; or
$R^7$ and $R^8$ together are alkylene or alkenylene, either of which may be substituted with $Z^1$, $Z^2$ and $Z^3$, completing a 3- to 8-membered saturated, unsaturated or aromatic ring together with the nitrogen atom to which they are attached;
$R^9$ is
  (a) hydrogen;
  (b) hydroxyl;
  (c) —C(O)H or —C(O)$R^6$;
  (d) —CO$_2R^6$;
  (e) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$; or
  (f) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
$R^{10}$ is
  (a) hydrogen;
  (b) —C(O)H or —C(O)$R^6$, except when $Z^5$ is —C(O)— and $R^9$ is —C(O)H, —C(O)$R^6$ or —CO$_2R^6$; or
  (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{11}$ is
(a) hydrogen;
(b) hydroxyl;
(c) —C(O)H, —C(O)$R^6$ or CO$_2R^6$; or
(d) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

or any two of $R^9$, $R^{10}$ and $R^{11}$ together are alkylene or alkenylene, either of which may be substituted with $Z^1$, $Z^2$ and $Z^3$, completing a 3- to 8-membered saturated, unsaturated or aromatic ring together with the atoms to which they are attached;

$Z^1$, $Z^2$ and $Z^3$ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(k) oxo;
(l) nitro;
(m) cyano;
(n) —C(O)H or —C(O)Z$^6$;
(o) —CO$_2$H or —CO$_2$Z$^6$;
(p) —Z$^4$—NZ$^7$Z$^8$;
(q) —Z$^4$—N(Z$^{11}$)—Z$^5$—Z$^6$; or
(r) —Z$^4$—N(Z$^{11}$)—Z$^5$—NZ$^7$Z$^8$;

$Z^4$ and $Z^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—; or
(g) —Z$^9$—O—C(O)—Z$^{10}$—;

$Z^6$, $Z^7$ and $Z^8$ are each independently hydrogen, alkyl, alkenyl, alkynyl, cycloalkyl, cycloalkylalkyl, cycloalkenyl, cycloalkenylalkyl, aryl or aralkyl, or $Z^7$ and $Z^8$ together are alkylene or alkenylene, completing a 3- to 8-membered saturated, unsaturated or aromatic ring together with the nitrogen atom to which they are attached;

$Z^9$ and $Z^{10}$ are each independently a single bond, alkylene, alkenylene or alkynylene;

$Z^{11}$ is
(a) hydrogen;
(b) hydroxyl;
(c) —C(O)H, —C(O)Z$^6$ or —CO$_2$Z$^6$; or
(d) alkyl, alkenyl, alkynyl, alkoxy, cycloalkyl, cycloalkylalkyl, cycloalkenyl, cycloalkenylalkyl, aryl or aralkyl;

or any two of $Z^7$, $Z^8$ and $Z^{11}$ together are alkylene or alkenylene, completing a 3- to 8-membered saturated, unsaturated or aromatic ring together with the atoms to which they are attached;

m is 1 or 2; and
n is 0, 1 or 2, or a pharmaceutically acceptable salt thereof.

2. The pharmaceutical composition of claim 1 wherein the additional therapeutic agent is selected from AII receptor antagonists, ACE inhibitors and NEP inhibitors.

3. A method of treating hypertension comprising administering to a patient in need thereof an effective amount of at least one endothelin antagonist in combination with an effective amount of at least one additional therapeutic agent selected from ECE inhibitors, PAP antagonists, angiotensin II receptor antagonists, renin inhibitors, ACE inhibitors, NEP inhibitors, HMG CoA reductase inhibitors, squalene synthetase inhibitors, bile acid sequestrants, calcium channel blockers, potassium channel activators, beta-adrenergic agents, antiarrhythmic agents, diuretics, and thrombolytic agents wherein said endothelin antagonist is selected from compounds of formula I

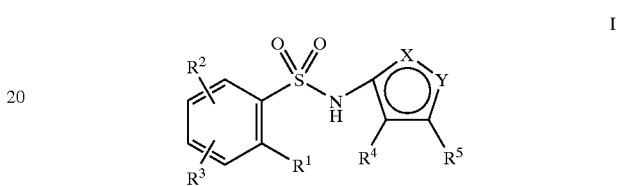

wherein:
one of X and Y is N and the other is O;
$R^1$, $R^2$ and $R^3$ are each independently
(a) hydrogen, except that $R^1$ is other than hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)R$^6$;
(h) —CO$_2$H or —CO$_2$R$^6$;
(i) —SH, —S(O)$_n$R$^6$, —S(O)$_m$—OH, —S(O)$_m$—OR$^6$, —O—S(O)$_m$—R$^6$, —O—S(O)$_m$OH or —O—S(O)$_m$—OR$^6$;
(j) —Z$^4$—NR$^7$R$^8$; or
(k) —Z$^4$—N(R$^{11}$)—Z$^5$—NR$^9$R$^{10}$;
wherein at least one of $R^1$, $R^2$ or $R^3$ is phenyl or biphenyl which may be substituted with $Z^1$, $Z^2$ and $Z^3$;

$R^4$ and $R^5$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)R$^6$;
(h) —CO$_2$H or —CO$_2$R$^6$;
(i) —SH, —S(O)$_n$R$^6$, —S(O)$_m$—OH, —S(O)$_m$—OR$^6$, —O—S(O)$_m$—R$^6$, —O—S(O)$_m$OH or —O—S(O)$_m$—OR$^6$;
(j) —Z$^4$—NR$^7$R$^8$; or
(k) —Z$^4$—N(R$^{11}$)—Z$^5$—NR$^9$R$^{10}$; or $R^6$ is alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^7$ is
- (a) hydrogen;
- (b) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;
- (c) cyano;
- (d) hydroxyl;
- (e) —C(O)H or —C(O)$R^6$;
- (f) —CO$_2R^6$;
- (g) —SH, —S(O)$_nR^6$, —S(O)$_m$—OH, —S(O)$_m$—O$R^6$, —O—S(O)$_m$—$R^6$, —O—S(O)$_m$OH or —O—S(O)$_m$—O$R^6$, except when $Z^4$ is —S(O)$_n$—;

$R^8$ is
- (a) hydrogen;
- (b) —C(O)H or —C(O)$R^6$, except when $Z^4$ is —C(O)— and $R^7$ is —C(O)H, —C(O)$R^6$ or —CO$_2R^6$;
- (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$; or $R^7$ and $R^8$ together are alkylene or alkenylene, either of which may be substituted with $Z^1$, $Z^2$ and $Z^3$, completing a 3- to 8-membered saturated, unsaturated or aromatic ring together with the nitrogen atom to which they are attached;

$R^9$ is
- (a) hydrogen;
- (b) hydroxyl;
- (c) —C(O)H or —C(O)$R^6$;
- (d) —CO$_2R^6$;
- (e) —SH, —S(O)$_nR^6$, —S(O)$_m$—OH, —S(O)$_m$—O$R^6$, —O—S(O)$_mR^6$, —O—S(O)$_m$OH or —O—S(O)$_m$—O$R^6$;
- (f) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{10}$ is
- (a) hydrogen;
- (b) —C(O)H or —C(O)$R^6$, except when $Z^5$ is —C(O)— and $R^9$ is —C(O)H, —C(O)$R^6$ or —CO$_2R^6$; or
- (c) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

$R^{11}$ is
- (a) hydrogen;
- (b) hydroxyl;
- (c) —C(O)H, —C(O)$R^6$ or CO$_2R^6$; or
- (d) alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$;

or any two of $R^9$, $R^{10}$ and $R^{11}$ together are alkylene or alkenylene, either of which may be substituted with $Z^1$, $Z^2$ and $Z^3$, completing a 3- to 8-membered saturated, unsaturated or aromatic ring together with the atoms to which they are attached;

$Z^1$, $Z^2$ and $Z^3$ are each independently
- (a) hydrogen;
- (b) halo;
- (c) hydroxy;
- (d) alkyl;
- (e) alkenyl;
- (f) aralkyl;
- (g) alkoxy;
- (h) aryloxy;
- (i) aralkoxy;
- (j) —SH, —S(O)$_nZ^6$, —S(O)$_m$—OH, —S(O)$_m$—O$Z^6$, —O—S(O)$_m$—$Z^6$, —O—S(O)$_m$OH or —O—S(O)$_m$—O$Z^6$;
- (k) oxo;
- (l) nitro;
- (m) cyano;
- (n) —C(O)H or —C(O)$Z^6$;
- (o) —CO$_2$H or —CO$_2Z^6$;
- (p) —$Z^4$—N$Z^7Z^8$;
- (q) —$Z^4$—N($Z^{11}$)—$Z^5$—$Z^6$; or
- (r) —$Z^4$—N($Z^{11}$)—$Z^5$—N$Z^7Z^8$;

$Z^4$ and $Z^5$ are each independently
- (a) a single bond;
- (b) —$Z^9$—S(O)$_n$—$Z^{10}$—;
- (c) —$Z^9$—C(O)—$Z^{10}$—;
- (d) —$Z^9$—C(S)—$Z^{10}$—;
- (e) —$Z^9$—O—$Z^{10}$—;
- (f) —$Z^9$—S—$Z^{10}$—; or
- (g) —$Z^9$—O—C(O)—$Z^{10}$—;

$Z^6$, $Z^7$ and $Z^8$ are each independently hydrogen, alkyl, alkenyl, alkynyl, cycloalkyl, cycloalkylalkyl, cycloalkenyl, cycloalkenylalkyl, aryl or aralkyl, or $Z^7$ and $Z^8$ together are alkylene or alkenylene, completing a 3- to 8-membered saturated, unsaturated or aromatic ring together with the nitrogen atom to which they are attached;

$Z^9$ and $Z^{10}$ are each independently a single bond, alkylene, alkenylene or alkynylene;

$Z^{11}$ is
- (a) hydrogen;
- (b) hydroxyl;
- (c) —C(O)H, —C(O)$Z^6$ or —CO$_2Z^6$; or
- (d) alkyl, alkenyl, alkynyl, alkoxy, cycloalkyl, cycloalkylalkyl, cycloalkenyl, cycloalkenylalkyl, aryl or aralkyl;

or any two of $Z^7$, $Z^8$ and $Z^{11}$ together are alkylene or alkenylene, completing a 3- to 8-membered saturated, unsaturated or aromatic ring together with the atoms to which they are attached;

m is 1 or 2; and n is 0, 1 or 2, or a pharmaceutically acceptable salt thereof.

4. The method of claim 3 wherein the additional therapeutic agent is selected from AII receptor antagonists, ACE inhibitors and NEP inhibitors.

* * * * *